United States Patent
Gillberg et al.

(10) Patent No.: US 10,864,228 B2
(45) Date of Patent: *Dec. 15, 2020

(54) ORAL CHOLESTYRAMINE FORMULATION AND USE THEREOF

(71) Applicant: Albireo AB, Gothenburg (SE)

(72) Inventors: Per-Göran Gillberg, Mölndal (SE); Nils Ove Gustafsson, Löddeköpinge (SE); Nils-Olof Lindberg, Limhamn (SE); Jessica Elversson, Dalby (SE)

(73) Assignee: Albireo AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/988,210

(22) Filed: May 24, 2018

(65) Prior Publication Data

US 2018/0360869 A1 Dec. 20, 2018

Related U.S. Application Data

(63) Continuation of application No. 15/449,779, filed on Mar. 3, 2017, which is a continuation of application No. PCT/SE2017/050128, filed on Feb. 9, 2017.

(30) Foreign Application Priority Data

Feb. 9, 2016 (SE) ........................ 1650157

(51) Int. Cl.
| | |
|---|---|
| *A61K 31/745* | (2006.01) |
| *A61K 9/50* | (2006.01) |
| *A61K 31/785* | (2006.01) |
| *A61K 9/00* | (2006.01) |
| *A61K 9/48* | (2006.01) |

(52) U.S. Cl.
CPC ............ *A61K 31/745* (2013.01); *A61K 9/009* (2013.01); *A61K 9/0053* (2013.01); *A61K 9/4833* (2013.01); *A61K 9/4866* (2013.01); *A61K 9/4891* (2013.01); *A61K 9/5047* (2013.01); *A61K 9/5073* (2013.01); *A61K 31/785* (2013.01)

(58) Field of Classification Search
CPC .... A61K 31/745; A61K 45/06; A61K 9/0053; A61K 9/009; A61K 9/4833; A61K 9/4866; A61K 9/4891; A61K 9/5047; A61K 9/5073
See application file for complete search history.

(56) References Cited

U.S. PATENT DOCUMENTS

| | | | |
|---|---|---|---|
| 3,539,380 A | 11/1970 | Johnson | |
| 4,172,120 A | 10/1979 | Todd et al. | |
| 4,507,235 A | 3/1985 | Wunsch | |
| 5,167,965 A | 12/1992 | Schulz | |
| 5,294,448 A * | 3/1994 | Ring | A61K 9/286 424/475 |
| 5,422,124 A | 6/1995 | Valducci | |
| 5,578,316 A | 11/1996 | Bhardwaj et al. | |
| 5,681,584 A | 10/1997 | Savastano | |
| 5,811,388 A | 9/1998 | Friend et al. | |
| 5,900,233 A | 5/1999 | Day | |
| 5,976,811 A | 11/1999 | Mullner et al. | |
| 5,994,391 A | 11/1999 | Lee et al. | |
| 6,069,167 A | 5/2000 | Sokol | |
| 6,277,831 B1 | 8/2001 | Frick et al. | |
| 6,346,527 B1 | 2/2002 | Takenaka et al. | |
| 6,355,672 B1 | 3/2002 | Yasuma et al. | |
| 6,387,924 B2 | 5/2002 | Lee et al. | |
| 6,387,944 B1 | 5/2002 | Frick et al. | |
| 6,426,340 B1 | 7/2002 | Gibson et al. | |
| 6,592,900 B1 | 7/2003 | Buhler | |
| 6,635,280 B2 | 10/2003 | Shell et al. | |
| 6,676,979 B2 | 1/2004 | Marlett et al. | |
| 6,906,058 B2 | 6/2005 | Starke et al. | |
| 6,943,189 B2 | 9/2005 | Keller et al. | |
| 7,019,023 B2 | 3/2006 | Frick et al. | |
| 7,125,864 B2 | 10/2006 | Starke et al. | |
| 7,132,416 B2 | 11/2006 | Starke et al. | |
| 7,132,557 B2 | 11/2006 | Wilkes et al. | |
| 7,192,945 B2 | 3/2007 | Starke et al. | |
| 7,192,946 B2 | 3/2007 | Starke et al. | |
| 7,192,947 B2 | 3/2007 | Starke et al. | |
| 7,226,943 B2 | 6/2007 | Starke et al. | |
| 7,238,684 B2 | 7/2007 | Starke et al. | |
| 7,514,421 B2 | 4/2009 | Abrahamsson et al. | |
| 7,767,229 B1 | 8/2010 | Milne et al. | |
| 7,923,468 B2 | 4/2011 | Frick et al. | |
| 7,939,061 B2 | 5/2011 | Prakash et al. | |
| 8,048,413 B2 | 11/2011 | Huguet | |
| 8,067,584 B2 | 11/2011 | Starke et al. | |
| 9,023,368 B2 | 5/2015 | Basit et al. | |
| 9,295,677 B2 | 3/2016 | Ling et al. | |
| 9,409,875 B2 | 8/2016 | Bohlin et al. | |
| 9,684,018 B2 | 6/2017 | Horanzy | |
| 9,694,018 B1 | 7/2017 | Gillberg et al. | |
| 9,701,649 B2 | 7/2017 | Bohlin et al. | |

(Continued)

FOREIGN PATENT DOCUMENTS

| | | |
|---|---|---|
| CA | 2065151 | 3/1991 |
| DE | 3930168 | 3/1991 |

(Continued)

OTHER PUBLICATIONS

U.S. Appl. No. 13/881,435, filed May 22, 2013, Gillberg et al.

(Continued)

*Primary Examiner* — Matthew P Coughlin
*Assistant Examiner* — Thurman Wheeler
(74) *Attorney, Agent, or Firm* — Fish & Richardson P.C.

(57) ABSTRACT

The invention relates to an oral formulation for targeted delivery of cholestyramine to the colon, comprising a plurality of cholestyramine pellets that are coated with a diffusion-controlled inner coating and an enteric outer coating. The invention also relates to the use of this formulation in the treatment of bile acid malabsorption.

30 Claims, 4 Drawing Sheets

(56) References Cited

U.S. PATENT DOCUMENTS

| | | |
|---|---|---|
| 9,745,276 B2 | 8/2017 | Bohlin et al. |
| 9,872,844 B2 | 1/2018 | Zernel et al. |
| 2002/0054903 A1 | 5/2002 | Tyler et al. |
| 2002/0142054 A1 | 10/2002 | Marlett et al. |
| 2003/0124088 A1 | 7/2003 | Masuda et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0089572 A1 | 4/2005 | Kumar |
| 2005/0113362 A1 | 5/2005 | Lindstedt et al. |
| 2005/0118326 A1 | 6/2005 | Anifinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2005/0282822 A1 | 12/2005 | Alstermark et al. |
| 2006/0083790 A1 | 4/2006 | Anderberg et al. |
| 2006/0210631 A1* | 9/2006 | Patel ............... A61K 9/2081 424/470 |
| 2006/0210633 A1 | 9/2006 | Dharmadhikari et al. |
| 2007/0197522 A1 | 8/2007 | Edwards et al. |
| 2007/0237818 A1 | 10/2007 | Malcom et al. |
| 2008/0193543 A1 | 8/2008 | Morello |
| 2008/0207592 A1 | 8/2008 | Frick et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2011/0003782 A1 | 1/2011 | Pellicciari |
| 2011/0152204 A1 | 6/2011 | Gedulin et al. |
| 2011/0159087 A1 | 6/2011 | Sathe et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0052269 A1* | 2/2013 | Lescure ............ A61K 9/1652 424/495 |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0030009 A1 | 6/2018 | Gillberg et al. |
| 2018/0264029 A1 | 9/2018 | Gillberg et al. |
| 2018/0264030 A1 | 9/2018 | Gillberg et al. |
| 2018/0264031 A1 | 9/2018 | Gillberg et al. |
| 2018/0360870 A1 | 12/2018 | Gillberg et al. |
| 2018/0360871 A1 | 12/2018 | Gillberg et al. |
| 2018/0362577 A1 | 12/2018 | Gillberg et al. |
| 2019/0046451 A1 | 2/2019 | Gillberg et al. |
| 2019/0367467 A1 | 12/2019 | Gillberg et al. |
| 2020/0002299 A1 | 1/2020 | Lundqvist |
| 2020/0046635 A1 | 2/2020 | Gillberg et al. |
| 2020/0046636 A1 | 2/2020 | Gillberg et al. |
| 2020/0046757 A1 | 2/2020 | Gillberg et al. |
| 2020/0046758 A1 | 2/2020 | Gillberg et al. |
| 2020/0049611 A1 | 2/2020 | Gillberg et al. |

FOREIGN PATENT DOCUMENTS

| | | |
|---|---|---|
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1273307 | 1/2003 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | A-2004-516285 | 6/2004 |
| JP | B-3665055 | 6/2005 |
| JP | 2006/124695 | 5/2006 |
| JP | B-4870552 | 2/2012 |
| JP | 2013-541584 | 11/2013 |
| JP | A-2013-542953 | 11/2013 |
| JP | B-5421326 | 2/2014 |
| JP | H02258719 | 10/2019 |
| WO | WO 1991/03249 | 3/1991 |
| WO | WO 93/16055 | 8/1993 |
| WO | WO 94/00111 | 1/1994 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | WO 98/03818 | 1/1998 |
| WO | WO 98/07449 | 1/1998 |
| WO | WO 98/38182 | 9/1998 |
| WO | WO 98/40375 | 9/1998 |
| WO | WO 1998/56757 | 12/1998 |
| WO | WO 99/01149 | 1/1999 |
| WO | WO 99/32478 | 1/1999 |
| WO | WO 99/35135 | 7/1999 |
| WO | WO 99/64409 | 7/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 2001/34570 | 5/2001 |
| WO | WO 01/60807 | 8/2001 |
| WO | WO 01/66533 | 9/2001 |
| WO | WO 01/68096 | 9/2001 |
| WO | WO 01/68637 | 9/2001 |
| WO | WO 02/08211 | 1/2002 |
| WO | WO 02/09815 | 4/2002 |

(56) References Cited

FOREIGN PATENT DOCUMENTS

| WO | WO 02/32428 | 4/2002 |
|---|---|---|
| WO | WO 02/50051 | 6/2002 |
| WO | WO 02/53548 | 6/2002 |
| WO | WO 03/020710 | 3/2003 |
| WO | WO 03/022286 | 3/2003 |
| WO | WO 03/022804 | 3/2003 |
| WO | WO 03/022825 | 3/2003 |
| WO | WO 03/022830 | 3/2003 |
| WO | WO 2003/043992 | 5/2003 |
| WO | WO 03/051821 | 6/2003 |
| WO | WO 03/051822 | 6/2003 |
| WO | WO 03/061663 | 7/2003 |
| WO | WO 03/091232 | 11/2003 |
| WO | WO 03/106482 | 11/2003 |
| WO | WO 04/006899 | 1/2004 |
| WO | WO 04/056748 | 7/2004 |
| WO | WO 04/076430 | 9/2004 |
| WO | WO 04/089350 | 9/2004 |
| WO | WO 04/020421 | 10/2004 |
| WO | WO 2004/089350 | 10/2004 |
| WO | WO 2005/082874 | 9/2005 |
| WO | WO 07/009655 | 1/2007 |
| WO | WO 07/009656 | 1/2007 |
| WO | WO 08/058628 | 5/2008 |
| WO | WO 08/058630 | 5/2008 |
| WO | WO 08/058631 | 5/2008 |
| WO | WO 10/062861 | 6/2010 |
| WO | WO 2010/041268 | 9/2010 |
| WO | WO 11/137135 | 11/2011 |
| WO | WO 11/150286 | 12/2011 |
| WO | WO 12/064267 | 5/2012 |
| WO | WO 12/064268 | 5/2012 |
| WO | WO 13/063512 | 5/2013 |
| WO | WO 13/063526 | 5/2013 |
| WO | WO 2014/174066 | 10/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |

OTHER PUBLICATIONS

U.S. Appl. No. 14/505,811, filed Oct. 3, 2014, Gillberg et al.
U.S. Appl. No. 15/230,124, filed Aug. 5, 2016, Gillberg et al.
U.S. Appl. No. 13/881,447, filed May 17, 2013, Gillberg et al.
U.S. Appl. No. 14/505,782, filed Oct. 3, 2014, Gillberg et al.
U.S. Appl. No. 15/069,355, filed Mar. 14, 2016, Gillberg et al.
U.S. Appl. No. 15/069,199, filed Mar. 14, 2016, Gillberg et al.
U.S. Appl. No. 15/276,446, filed Sep. 26, 2016, Gillberg et al.
U.S. Appl. No. 15/726,071, filed Oct. 5, 2017, Gillberg et al.
U.S. Appl. No. 15/722,110, filed Oct. 2, 2017, Gillberg et al.
U.S. Appl. No. 15/726,203, filed Oct. 5, 2017, Gillberg et al.
U.S. Appl. No. 15/894,472, filed Feb. 12, 2018, Gillberg et al.
U.S. Appl. No. 15/976,584, filed May 10, 2018, Gillberg et al.
U.S. Appl. No. 15/134,583, filed Apr. 21, 2016, Bohlin et al.
U.S. Appl. No. 15/134,586, filed Apr. 21, 2016, Bohlin et al.
U.S. Appl. No. 15/449,645, filed Mar. 3, 2017, Gillberg et al.
U.S. Appl. No. 15/988,560, filed May 24, 2018, Gillberg et al.
U.S. Appl. No. 15/988,688, filed May 24, 2018, Gillberg et al.
U.S. Appl. No. 15/449,781, filed Mar. 3, 2017, Gillberg et al.
U.S. Appl. No. 15/988,281, filed May 24, 2018, Gillberg et al.
U.S. Appl. No. 15/988,317, filed May 24, 2018, Gillberg et al.
U.S. Appl. No. 15/449,779, filed Mar. 3, 2017, Gillberg et al.
U.S. Appl. No. 15/988,202, filed May 24, 2018, Gillberg et al.
U.S. Appl. No. 15/519,808, filed Apr. 17, 2017, Ymen et al.
U.S. Appl. No. 15/320,651, filed Dec. 20, 2016, Ando et al.
U.S. Appl. No. 15/320,621, filed Dec. 20, 2016, Ando et al.
"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001&rank=7, 4 pages.
"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.
"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.
"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.
"An Extension Study to Evaluate the Long-Term Safety and Durability of Effect of LUM001 in the Treatment of Cholestatic Liver Disease in Subjects With Alagille Syndrome (IMAGINE-II)," Clincal Trials.gov, Apr. 16, 2014, retrieved on Oct. 3, 2014, http://clinicaltrials.gov/ct2/show/NCT02117713?term=LUM001&rank=2, 3 pages.
"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
"EASL Clinical Practice Guidelines: Management of cholestatic liver diseases," European Assoc. for the Study of the Liver, Journal of Hepatology, 2009, 51:237-267.
"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.
"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.
"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.
"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.
"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.
"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.
"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.
"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.
"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.

(56) References Cited

OTHER PUBLICATIONS

AASLD: 2017 68th Annual Meeting of the American Association for the Study of Liver Diseases, Washington, DC, Oct. 20-24, 2017, (Abstract only).
Alissa et al., "Invited Review: Update on Progressive Familial Intrahepatic Cholestasis," *Journal of Pediatric Gastroenterology and Nutrition*, 2008, 46:241-252.
Alonso et al., "Histologic pathology of the liver in progressive familial intrahepatic cholestasis," Journal of Pediatric Gastroenterology and Nutrition, 14: 128-133, 1994.
Alvarez, Fernando; "Treatments in chronic cholestasis in children." Ann. Nestlé (2008) 66 p. 127-135.
American Diabetes Association, "Management of Dyslipidemia in Adults with Diabetes," Diabetes Care, Jan. 2003, 26(1).
Anakk et al., "Bile acids activate YAP to promote liver carcinogenesis," Cell Rep., Nov. 27, 2013, 5(4):1060-1069.
Angulo et al., "Independent Predictors of Liver Fibrosis in Patients With Nonalcoholic Steatohepatitis," Hepatology, Dec. 1999, 30(6): 1356-1362.
Angulo, "Use of ursodeoxycholic acid in patients with liver disease," *Current Gastroenterology Reports*, Feb. 1, 2002, 4(1):37-44.
Artursson and Karlsson, "Corresslation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibito A4250 protects against bile acid-mediated cholestatic liver injury in mice," J. Hepatology, 2014, 60:S57.
Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Balbach et al., "Pharmaceutical evaluation of early development candidates "The 100 mg-approach"," Int J Pharm, May 4, 2004, 275(1):1☐12.
Banker et al., "Modern Pharmaceutics, 3ed", Marcel Dekker, New York, 1996, pp. 451 and 596.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Bavin, "Polymorphism in Process Development," Chemistry and Industry, 527-529, 1989.
Beraza et al., Nor-ursodeoxycholic acid reverses hepatocyte-specific nemo-dependnt steatohepatitis. Gut, 2011: 60: 387-396.
Billington et al., "Effects of bile salts on the plasma membranes of isolated rat hepatocytes," Bichem. J. 188: 321-327, 1980.
Board of Appeal of European Patent Office, Case No. T 077/08-3. 3.01, dated May 24, 2011, 17 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Brunt et al., "Nonalcoholic Steatohepatitis: A Proposal for Grading and Staging the Histological Lesions," American Jounral of Gastroenterology, Sep. 1999, 94(9): 2467-2474.
Brunzell and Hokanson, "Dislipidemia of Central Obesity and Insulin Resistance," Diabetes Care, 1999, 22(Suppl. 3):C10-C13.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.

Byrn et al., "Pharmaceutical Solids: A Strategic Approach to Regulatory Considerations," Pharmaceutical Research, 1995, 12(7), pp. 945-954.
Caira, "Crystalline Polymorphism of Organic Compounds," in: Topics in Current Chemistry, Jan. 1998, 198:163☐208.
Carulli et al, "Review article: effect of bile salt pool composition on hepatic and biliary functions," Aliment. Pharmacol. Ther. 2000, vol. 14, suppl. 2, p. 14-18.
Chen et al., "Bile salt export pump is dysregulated with altered farnesoid X receptor isoform expression in patients with hepatocelular carcinoma," Hepatologu, 57: 4, 1530-1541, 2013.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chen et al., "Serum and urine metabolite profiling reveals potential biomarkers of human hepatocellular carcinoma," Molecular and Cellular Proteomics 10.7, 2011.
Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.
Chourasia et al., "Polysaccharides for colon targeted drug delivery," Drug Delivery, Academic Press, vol. 11, No. 2, Jan. 1, 2004, 129-148, XP008060983.
Das & Kar., Non alcoholic steatohepatitis. JAPI. 53:, Mar. 2005.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," *Hepatology: Autoimmune, Cholestatic and Biliary Disease*, May 2010, 1645-1655.
Davit-Spraul et al., "Progressive familial intrahepatic cholestasis," *Orphanet Journal of Rare Diseases*, Jan. 2009, 4:1-12.
Dawson et al., "Bile acid transporters" J. Lipid Res. 2009, 50, 2340-2357.
DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.
Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract Only).
Dongiovanni et al., "Genetic Predisposition in NAFLD and NASH: Impact on Severity of Liver Disease and Response to Treatment," Curren Pharma Design, 2013, 19:5219-5238.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Espenshade and Hughes, "Regulation of Sterol Synthesis in Eukaryotes," Annu. Rev. Genet., 2007, 41:401-427.
Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS3OD_Promotiondatasheet_09072008.
Extended European Search Report in European Application No. 11840392.2, dated Feb. 24, 2014, 7 pages.
Extended European Search Report in European Application No. 11840481.3, dated Feb. 13, 2014, 10 pages.
Faubion et al., "Toxic bile salts induce rodent hepatocyte apoptosis via direct activation of Fas," The Journal of Clinical Investigation, 103: 1, 137-145, 1999.
Forner et al., "Treatment of hepatocellular carcinoma," Critical Reviews in Oncology/Hematology, 2006, 60:89-98.

(56) References Cited

OTHER PUBLICATIONS

Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "The IBAT Inhibition by A3309 ☐ A Potential Mechanism for the Treatment of Constipation," Gastroenterology, 2010, 138(5), Supp 1, S-224.
Glasgov et al., "Compensatory enlargement of human atherslcerotic coronary arteries," N Engl. J. Med., May 1987, 316(22):1371-1375 (Abstract Only).
Govers et al., "Characterization of the adsorption of conjugated and unconjugated bile acids to insoluble, amorphous calcium phosphate", Journal of Lipid Research 35(5):741-748, 1994.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.
Heathcote, "Management of primary biliary cirrhosis," Hepatology, 2000, 31(4):1005-1013.
hepc.liverfoundation.org [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf, 8 pages.
Higaki et al., "Inhibition of ileal na+/bile acid cotranporter by S-8921 reduces serum cholesterol and prevents atherosclerosis in rabbits", Arteriosclerosis, Thrombosis, and Vascular Biology 18(8):1304-1311, 1998.
Hollands et al., "Ileal exclusion for Byler's disease: an alternative surgical approach with promising early results for pruritis,"Journal of Pediatric Surgery, Feb. 1988, 33(2): 220-224.
Huang et al., "Discovery of Potent, Nonsystemic Apical Sodium-Codependent Bile Acid Transporter Inhibitors (Part 2)," J. Med. Chem., 2005, 48:5853-5868.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for Application No. PCT/SE2017/050126, dated Apr. 24, 2017, 27 pages.
International Search Report and Written Opinion for Application No. PCT/SE2017/050127, dated May 8, 2017, 16 pages.
International Search Report and Written Opinion for Application No. PCT/SE2017/050128, dated May 8, 2017, 16 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12pages.
International Search Report and Written Opinion for International Application No. PCT/SE2011/051336, dated Feb. 22, 2012, 18 pages.
International Search Report, Application No. PCT/JP2015/068240, dated Sep. 15, 2015, 11 pages (with English translation).
Ishibashi et al., "Hypercholesterolemia in low density lipoprotein receptor knockout mice and its reversal by adenovirus-mediated gene delivery", Journal of Clinical Investigation 92(2):883-893, 1993.
Islam and Di Baise, "Bile Acids: An underrecognized and underappreciated cause of chronic diarrhea," Pract. Gastroenterol. 2012, vol. 36(10), p. 32-44.
Jacobsen et al., "Effect of enterocoated cholestyramine on bowel habit after ileal resection: a double blind crossover study," Br. Med. J. 1985, vol. 290, p. 1315-1318.
Jacquet et al., "Alagille Syndrome in Adult Patients: It is Never Too Late," *American Journal of Kidney Diseases*, May 2007, 49(5):705-709.
Jansen et al., "Endogenous bile acids as carcinogens," Journal of Hepatology, Sep. 2007, 47(3):434-435.
Jiang et al., "Non alcoholic steatohepatitis a precursor for hepatocellular carcinoma development," World Journal of Gastroenterology: WJG, Nov. 28, 2014, 20(44):16464-16473.
Knisely et al., "Hepatocellular Carcinoma in ten children under five years of age with bile salt export pump deficiency," Hepatology, Aug. 2006, 44(2):478-486.
Korman et al., "Assessment of Activity in Chronic Active Liver Disease," New England Journal of Medicine, 2010, 290(25):1399-1402.
Kumar and Tandon, "Use of ursodeoxycholic acid in liver diseases," J. Gastroenterology and Hepatology, 2001, 16:3-14.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Kurbegov et al., Biliary diversion for progressive familial intrahepatic cholestasis: Improved liver morphology and bile acid profile, Gastroenterology, 125: 4, 1227-1234, 2003.
Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.
Lewis et al., "Effects of 2164U90 on ileal bile acid adsorption and serum cholesterol in rats and mice", Journal of Lipid Research 36(5):1098-1105, 1995.
Ling, "Congenital cholestatic syndromes: What happens when children grow up?," Can J Gastroenterol, Nov. 11, 2007, 21(11):743-751.
Longo et al., "Hyperlipidemia in chronic cholestatic liver disease," Curr. Treat. Options Gastrenterol., 2001, 4:111-114.
Lykavieris et al., "Outcome of liver disease in children with Alagille syndrome: a study of 163 patients," Gut, 2001, 49:431-435.
Marzorati et al, "A novel hypromellose capsule, with acid resistance properties, permits the targeted delivery of acid-sensitive products to the intestine, " LWT—Food Sci. Techno.l 2015, vol. 60, p. 544-551.
MerckManuals.com, "Obesity," 2008, Merch Manual for Health Care Professionals, Section—Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Morissette et al., "High-throughput crystallization: polymorphs, salts, co-crystals and solvates of pharmaceutical solids," Advanced Drug Delivery Reviews, 2004, 56:275-300.
Mouzaki and Allard, "Non-alcoholic steatohepatitis: the therapeutic challenge of a global epidemic," Annals of Gastroenterology, 2012, 25: 207-217.
Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.

(56) References Cited

OTHER PUBLICATIONS

Pattni and Walters, "Recent advances in the understanding of bile acid malabsorption," Br. Med. Bull. 2009, vol. 92, p. 79-93.
Perez et al., "Bile-acid-induced cell injury and protection," World J Gastroenterol, Apr. 2009, 15(14)1677-1689.
Perumpail et al., "Clinical epidemiology and disease burden of nonalcoholic fatty liver disease," World Journal of Gastroenterology, Dec. 2017, 23(47): 8263-8276.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Possemiers et al, "PCR-DGGE-based quantification of stability of the microbial community in a simulator of the human intestinal microbial ecosystem," FEMS Microbiol. Ecol. 2004, vol. 49, p. 495-507.
Poupon et al., "Chronic Cholestatic Disease," J. Hepatology, 2000, 32(1):12-140.
Qiu et al., "Disruption of BSEP function in HepaRG cells alters bile acid disposition and is a susceptive factor to drug-induced cholestatic injury," Mol. Pharmaceutics, 13:4,, 2016 (Abstract only).
Report EC20082069.02.01 dated Feb. 2009, filed with appellant's letter of Apr. 26, 2011.
Report filed at oral proceedings before opposition division, GMS-CFEP-2007-20, "Filtration and Drying Study on Amorphous and Form IV Atorvastatin Calcium," 2007.
Rolo et al., "Bile acids affect liver mitochondrial bioenergetics: Possible relevance for cholestasis therapy," Toxocological Sciences, 57: 177-185, 2000.
Satapathy and Sanyal, "Epidemiology and Natural History of Non-alcoholic Fatty Liver Disease," Seminars in Liver Disease, Aug. 2015, 35(3): 221-235.
Scheuer, "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Shah et al., "Role of Caco-2 Cell Monolayers in Prediction of Intestinal Drug Absorption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Singhal et al., "Drug polymorphism and dosage form design: a practical perspective," Adv Drug Deliv Rev, Feb. 23, 2004, 56(3):335□347.
Sinha and Kumria, "Microbially triggered drug delivery to the colon," Eur. J. Pharm. Sci. 2003, vol. 18, p. 3-18.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Staels and Kuipers, "Bile Acid Sequestrants and the Treatment of Type 2 Diabetes Mellitus," Drugs, 2007, 67(10):1383-1392.
Stein, "Managing Dyslipidemia in the High-Risk Patient," Am J. Cardiol., 2002, 89:50-57.
Sun et al., "Bile acids promote diethylnitrosamine-induced hepatocellular carcinoma via increased inflammatory signaling," American Journal of Physiology-Gastrointestinal and Liver Physiology, May 5, 2016, 311(1):G91-104.
Tanaka et al., "Genetic and Familial considerations of Primary Biliary Cirrhosis," Am. J. Gastroenterology, 2001, 96(1): 8-15.
Tollefson et al., "A novel class of apical sodium co-dependent bile acid transporter inhibitors: the 1,2-Benzothiazepines", Bioorganic and Medicinal Chemistry Letters 12:3727-3730, 2003.

Tremont et al., "Discovery of Potent, Nonsystemic Apical Sodium-Codependent Bile Acid Transporter Inhibitors (Part 1)," J. Med. Chem, 2005, 48:5837-5852.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Tilberg et al., "Na+-dependent bile acid transport in the ileum: the balance between diarrhea and constipation", Gastroenterology 98(1):25-32, 1989.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Watts and Illum, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.
Whitington et al., "Partial external diversion of bile for the treatment of intractable pruritus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Woolbright et al., "Novel insight into mechanisms of cholestatic liver injury," World Journal of Gastroenterology, 18: 36, 4985-4993, 2012.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zhang et al., "Effect of bile duct ligation on bile acid composition in mouse serum and liver," Liver int, 32: 1, 58-69, 2012.
Zhang et al., Abcbl 1 deficiency induces cholestasis coupled to impaired B-Fatty acid oxidation in mice, Journal of biological chemistry, 287: 29, 24784-2479, 2012.
"Appleby et al., ""Effects of conventional and a novel colonic-release bile acid sequestrant, A3384, on fibroblast growth factor 19 and bile acid metabolism in healthy volunteers and patients with bile acid diarrhoea""", United Eur. Gastroent. J., vol. 5, pp. 380-388, 2017".
DiBaise et al., "Bile Acids: An Underrecognized and Underappreciated Cause of Chronic Diarrhea", Pract. Gastroenterol. vol. 36(10), p. 32-44, 2012.
International Search Report and Written Opinion in International Application No. PCT/SE2018/050802, dated Oct. 26, 2018.
International Search Report and Written Opinion in International Application No. PCT/SE2018/050803, dated Oct. 26, 2018.
"Li et al., ""Effect of Resistant Starch Film Properties on the Colon-Targeting Release of Drug From Coated Pellets""", 152 J Control. Rel. e5, 2011".
McCullough et al., "The epidemiology and risk factors of NASH.", Blackwell Publishing, Chapter 3, 2005.
Adams et al., "Hepascore: an accurate validated predictor of liver fibrosis in chronic hepatitis C infection," Clin. Chem. 2005, vol. 51(10), p. 1867-1873.

(56) References Cited

OTHER PUBLICATIONS

Alashkar et al., "Meeting Info: 57th Annual Meeting of the AmericanSociety-of-Hematology," Orlando, FL, USA. Dec. 5-8, 2015, Amer Soc Hematol, Blood, 2015, 126(23).
Allison et al., "Studies on mixed populations of human intestinal bacteria grown in single-stage and multistage continuous culture systems," Appl. Environ. Microbial. 1989, 55(3):672-678.
Alvarez et al., "Reduced hepatic expression of farnesoid X receptor in hereditary cholestasis associated to mutation in ATP8B1," Hum Mol Genet, 2004, 13(20):2451-2460.
Angulo et al., "The NAFLD fibrosis score: a noninvasive system that identifies liver fibrosis in patients with NAFLD," Hepatology, 2007, vol. 45(4), p. 846-54.
Anzivino et al., "ABCB4 and ABCB11 mutations in intrahepatic cholestasis of pregnancy in an Italian population," Dig Liver Dis., 2013, 45(3):226-232.
Arnell et al., "Follow-up in children with progressive familial intrahepatic cholestasis after partial external biliary diversion," J Pediatr Gastroenterol Nutr., 2010, 51(4):494-499.
Beausejour et al., "Description of two new ABCB11 mutations responsible for type 2 benign recurrent intrahepatic cholestasis in a French-Canadian family," Can J Gastroenterol., 2011, 25(6):311-314.
Bhaskaran et al., "Extrusion Spheronization—A Review," International Journal of PharnnTech Research. vol. 2, No. 4, pp. 2429-2433, Oct.-Dec. 2010 (Year: 2010).
Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Bounford. University of Birmingham Dissertation Abstracts International, (2016) vol. 75, No. 1C. Order No. AA110588329. ProQuest Dissertations & Theses.
Burrows, "Interventions for treating cholestasis in pregnancy," Cochrane Database Syst. Rev., 4:CD00493, 2001.
Byrne et al., "Missense mutations and single nucleotide polymorphisms in ABCB11 impair bile salt export pump processing and function or disrupt pre-messenger RNA splicing," Hepatology., 2009, 49(2):553-567.
Camilleri, "Probiotics and irritable bowel syndrome: rationale, putative mechanisms, and evidence of clinical efficacy," Clin. Gastroenterol., 40(3):264-9, Mar. 2006.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chiang, "Bile acids: regulation of synthesis," J. Lipid Res, 2009, 50(10):1955-1966.
Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platform," PLoS One, 2017, 12(6):e0179200.
Davit-Spraul et al., "Liver transcript analysis reveals aberrant splicing due to silent and intronic variations in the ABCB11 gene," Mol Genet Metab., 2014, 113(3):225-229.
Dawson, "Role of the intestinal bile acid transporters in bile acid and drug disposition," Handb. Exp. Pharmacol. 2011, 201:169-203.

De Lédinghen et al., "Controlled attenuation parameter for the diagnosis of steatosis in non-alcoholic fatty liver disease," J Gastroenterol Hepatol., 2016, 31(4):848-855.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-Invasive Quantitative Assessment of Liver Fat by Ultrasound Imaging," Ultrasound Med Biol., 2018, 44(8):1585-1596.
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drugs as inhibitors of the human sodium taurocholate cotransporting polypeptide (NTCP).," Mol. Pharm. 2013, 10(3):1008-1019.
Drage et al., "Exon-skipping and mRNA decay in human liver tissue: molecular consequences of pathogenic bile salt export pump mutations," Sci Rep., 2016, vol. 6: 24827.
Drage et al., "Sequencing of FIC1, BSEP and MDR3 in a large cohort of patients with cholestasis revealed a high number of different genetic variants," J Hepatol. 2017, 67(6):1253-1264.
Droge et al., Zeitschrift fur Gastroenterologie 2015, 53(12) Abstract Number: A3-27. Meeting Info: 32. Jahrestagung der Deutschen Arbeitsgemeinschaft zum Studium der Leber. Dusseldorf, Germany. Jan. 22, 2016-Jan. 23, 2016.
Drumond et al., "Patients' appropriateness, acceptability, usability and preferences for pharmaceutical preparations: Results from a literature review on clinical evidence," Int. J. Pharm. 2017, 521(1-2):294-305.
Einspahr et al., "Protective role of wheat bran fiber: data from marker trials," Am. J. Med., 106(1A):32s-37s, Jan. 1999.
Ellinger et al., "Partial external biliary diversion in bile salt export pump deficiency: Association between outcome and mutation," World J Gastroenterol., 2017, 23(29):5295-5303.
Ellis et al., "Zebrafish abcb 1 1b mutant reveals strategies to restore bile excretion impaired by bile salt export pump deficiency," Hepatology, 2018, 67(4)1531-1545.
Engelen et al., "Oral size perception of particles: effect of size, type, viscosity and method," J. Text. Studies 2005, 36(4):373-386.
Evason et al., "Morphologic findings in progressive familial intrahepatic cholestasis 2 (PFIC2): correlation with genetic and immunohistochemical studies," Am J Surg Pathol., 2011, 35(5):687-696.
Ferreira et al., Pediatric Transplantation 2013, 17(Suppl. 1):99. Abstract Number: 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Francalanci et al., "Progressive familial intrahepatic cholestasis: Detection of new mutations and unusal modality of transmission," Digestive and Liver Disease 2010, 42(Suppl. 1):516, Abstract No. T.N.5.
Francalanci et al., Laboratory Investigation 2011, vol. 91, Supp. Suppl. 1, pp. 360A. Abstract No. 1526.
Fuentes-Zaragoza al., "Resistant Starch as functional ingredient: A review", , Food Research International, 43, 931-942, 2010.
Fuller, "Probiotics in man and animals," Appl. Bacterial. 1989, 66(5):365-378.
Gao et al., "Detection of hepatitis in children with idiopathic cholestatic bile salt export pump gene mutations," Shandong Yiyao, 2012, 52(10):14-16.
Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.
Gibson and Roberfroid, "Dietary modulation of the human colonic microbiota: introducing the concept of prebiotics," J. Nutr. 1995, 125(6):1401-1412.

(56) References Cited

OTHER PUBLICATIONS

Giovannoni et al., "Genetics and Molecular Modeling of New Mutations of Familial Intrahepatic Cholestasis in a Single Italian Center," PLoS One, 2015, 10(12):e0145021.

Goldschmidt et al., "Increased frequency of double and triple heterozygous gene variants in children with intrahepatic cholestasis," Hepatol Res., 2016, 46(4):306-311.

Griffin, et al., "A novel gene mutation in ABCB11 in siblings with progessive familial intrahepatic cholestasis type 2," Canadian Journal of Gastroenterology and Hepatology 2016, vol. 2016. Abstract No. A200. Meeting Info: 2016 Canadian Digestive Diseases Week, CDDW 2016. Montreal, QC, United States. Feb. 26, 2016-Feb. 29, 2016.

Gunaydin et al., "Progressive familial intrahepatic cholestasis: diagnosis, management, and treatment," Hepat Med., 2018, 10:95-104.

Guorui et al., "Genetic diagnosis of progressive familial intrahepatic cholestasis type 2," Linchuang Erke Zazhi, 2013, 31(10):905-909.

Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.

Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.

Hasegawa et al., "Intractable itch relieved by 4-phenylbutyrate therapy in patients with progressive familial intrahepatic cholestasis type 1," Orphanet J Rare Dis., 2014, 9:89.

Hayashi et al., "Assessment of ATP8B1 Deficiency in Pediatric Patients With Cholestasis Using Peripheral Blood Monocyte-Derived Macrophages," EBioMedicine, 2018, 27:187-199.

Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.

Herbst et al., "Taking the next step forward—Diagnosing inherited infantile cholestatic disorders with next generation sequencing," Mol Cell Probes, 2015, 29(5):291-298.

Ho et al., "Polymorphic variants in the human bile salt export pump (BSEP; ABCB11): functional characterization and interindividual variability," Pharmacogenet Genomics, 2010, 20(1):45-57.

Hoffman et al., Human Anatomy, picture of the colon, p. 1-7, https://www.webmd.com/digestive-disorders/picture-of-the-colon #1, Accesses Aug. 4, 2019.

Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.

Holz et al., "Plasma separation and anion adsorption results in rapid improvement of nasobiliary drainage (NBD)—refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie—10. Herbsttagung derDeutschen Gesellschaft fur Allgemein—und Viszeralchirurgie. Hamburg, Germany. Sep. 21, 2016-Sep. 24, 2016.

Hsu et al., "Adult progressive intrahepatic cholestasis associated with genetic variations in ATP8B1 and ABCB11," Hepatol Res., 2009, 39(6):625-631.

Hu et al., "Diagnosis of ABCB11 gene mutations in children with intrahepatic cholestasis using high resolution melting analysis and direct sequencing," Mol Med Rep., 2014, 10(3):1264-1274.

Imagawa et al., "Clinical phenotype and molecular analysis of a homozygous ABCB11 mutation responsible for progressive infantile cholestasis," J Hum Genet. 2018, 63(5):569-577.

Imagawa et al., "Generation of a bile salt export pump deficiency model using patient-specific induced pluripotent stem cell-derived hepatocyte-like cells," Sci Rep., 2017, 7:41806.

Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016.

International Search Report and Written Opinion for Appln. No. PCT/EP2019/064602, dated Aug. 9, 2019, 11 pages.

Ishak et al., "Histological grading and staging of chronic hepatitis," J. Hepatol. 1995, vol. 22, p. 696-699.

Ivashkin et al., "A novel mutation of ATP8B1 gene in young patient with familial intrahepatic cholestasis.," Hepatology International 2016, 10(1):S461, Abstract No. LBO-38. Meeting Info: 25th Annual Conference of the Asian Pacific Association for the Study of the Liver, APASL 2016. Tokyo, Japan. Feb. 20, 2016-Feb. 24, 2016.

Jankowska et al., "[Cholestatic liver disease in children]," Przegl. Epidemiol., 56:16-21, 2002.

Jankowska et al., "Ileal exclusion in children with progressive familial intrahepatic cholestasis," Pediatr Gastroenterol Nutr. 2014,58(1):92-95.

Jaquotot-Haerranz et al., "Clinical variability of mutations in the ABCB11 gene: a case report," Rev Esp Enferm Dig., 2013, 105(1):52-54.

Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.

Jirsa et al., "Indel in the FIC1/ATP8B1 gene—a novel rare type of mutation associated with benign recurrent intrahepatic cholestasis," Hepatol Res. 2004, 30(1):1-3.

Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.

Kang et al., "Progressive Familial Intrahepatic Cholestasis in Korea: A Clinicopathological Study of Five Patients," J Pathol Transl Med. May 16, 2019, 53(4):253-260.

Karpen and Dawson, "Not all (bile acids) who wander are lost: the first report of a patient with an isolated NTCP defect," Hepatology, 2015, 61(1):24-27.

Khosla et al., "Recurrent Post-partum Jaundice: Rare Genetic Disorder With Novel Genetic Mutations Identified," American Journal of Gastroenterology 2015, 110(1):S397. Meeting Info: 80th Annual Scientific Meeting of the American-College-of-Gastroenterology. Honolulu, HI, USA. Oct. 16-21, 2015.

Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Kooistra, et al., "KLIFS: A structural kinase-ligand interaction database," Nucleic Acids Res. 2016, 44(D1):D365-D371.

Kooistra, et al., "KLIFS: A structural kinase-ligand interaction database," Nucleic Acids Res., 2016, vol. 44, No. D1, pp. D365-D371.

Kosters et al., "Bile acid transporters in health and disease," Xenobiotica 2008, 38(7-8):1043-1071.

Kozarewicz, "Regulatory perspectives on acceptability testing of dosage forms in children," Int. J. Pharm. 2014, 469(2):245-248.

(56) References Cited

OTHER PUBLICATIONS

Krawczyk et al., "Prolonged cholestasis triggered by hepatitis A virus infection and variants of the hepatocanalicular phospholipid and bile salt transporters," Ann Hepatol., 2012, 11(5):710-744.
Lam et al., "A patient with novel ABCB11 gene mutations with phenotypic transition between BRIC2 and PFIC2," J Hepatol. 2006, 44(1):240-242.
Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.
Lang et al,. "Genetic variability, haplotype structures, and ethnic diversity of hepatic transporters MDR3 (ABCB4) and bile salt export pump (ABCB11)," Drug Metab Dispos. 2006, 34(9):1582-1599.
Lang et al., "Mutations and polymorphisms in the bile salt export pump and the multidrug resistance protein 3 associated with drug-induced liver injury," Pharmacogenet Genomics, 2007, 17(1):47-60.
Lee et al., "Early Diagnosis of ABCB11 Spectrum Liver Disorders by Next Generation Sequencing," Pediatr Gastroenterol Hepatol Nutr. 2017, 20(2):114-123.
Li et al., "ATP8B1 and ABCB11 mutations in Chinese patients with normal gamma-glutamyl transferase cholestasis: Phenotypic differences between progressive familial intrahepatic cholestasis type 1 and 2," Hepatology International 2017, 11(1):5180. Abstract No. OP284.
Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China. Feb. 15, 2017-Feb. 19, 2017.
Lichtinghagen R, et al., "The Enhanced Liver Fibrosis (ELF) score: normal values, influence factors and proposed cut-off values," J Hepatol. Aug. 2013;59(2):236-42.
Lin et al., "[Clinical and genetic analysis of an infant with progressive familial intrahepatic cholestasis type II].," Zhongguo Dang Dai Er Ke Za Zhi. 2018, 20(9)758-764 (with English abstract).
Liu et al., "ABCB11 gene mutations in Chinese children with progressive intrahepatic cholestasis and low gamma glutamyltransferase," Liver International 2010, 30(6):809-815.
Liu et al., "Association of variants of ABCB11 with transient neonatal cholestasis," Pediatr Int. 2013, 55(2):138-144.
Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.
Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver. Hong Kong, China. Feb. 13, 2009-Feb. 16, 2009.
Liu et al., "Homozygous p.Ser267Phe in SLC10A1 is associated with a new type of hypercholanemia and implications for personalized medicine," Scientific Reports, 2017, 7:9214.
Liu, et al., "Patient-centered pharmaceutical design to improve acceptability of medicines: similarities and differences in pediatric and geriatric populations," Drugs 2014, 74(16):1871-1889.
Lopez et al., "Effect of formulation variables on oral grittiness and preferences of multiparticulate formulations in adult volunteers," Eur. J. Pharm. Sci. 2016, 92:156-162.
Lv et al., "Noninvasive Quantitative Detection Methods of Liver Fat Content in Nonalcoholic Fatty Liver Disease," J Clin Transl Hepatol. 2018, 6(2):217-221.
Maggiore et al., "Relapsing features of bile salt export pump deficiency after liver transplantation in two patients with progressive familial intrahepatic cholestasis type 2," J Hepatol. 2010, 53(5):981-6.

Manghat and Wierzbicki, "Colesevelam hydrochloride: a specifically engineered bile acid sequestrant," Future Lipidology, 3(3):237-255, Jun. 2008.
Masahata et al., "Recurrence of Progressive Familial Intrahepatic Cholestasis Type 2 Phenotype After Living-donor Liver Transplantation: A Case Report," Transplant Proc. 2016, 48(9):3156-3162.
Matte et al., "Analysis of gene mutations in children with cholestasis of undefined etiology," J Pediatr Gastroenterol Nutr. 2010, 51(4):488-493.
McKay et al., "Mutation detection in cholestatic patients using microarray resequencing of ATP8B1 and ABCB11 [version 2; peer review: 2 approved, 1 approved with reservations]," F1000 Res., 2013, 2:32.
McMichael and Potter, "Reproduction, endogenous and exogenous sex hormones, and colon cancer: a review and hypothesis," J. Natl. Cancer Inst., 65(6):1201-07, Dec. 1980.
McPherson et al., "Simple non-invasive fibrosis scoring systems can reliably exclude advanced fibrosis in patients with non-alcoholic fatty liver disease," Gut 2010, 59(9):1265-9.
Miloh et al., Gastroenterology 2006, vol. 130, No. 4, Suppl. 2, pp. A759-A760. Meeting Info.: Digestive Disease Week Meeting/107th Annual Meeting of the American-Gastroenterological Association. Los Angeles, CA, USA. May 19.
Minekus et al., "A computer-controlled system to simulate conditions of the large intestine with peristaltic mixing, water absorption and absorption of fermentation products," Appl. Microbiol Biatechnol. 1999, 53(1):108-114.
Mishra et al., "Investigation of organoleptic characteristics in the development of soft chews of calcium carbonate as mineral supplement," Yakugaku Zasshi 2009, 129(12):1537-1544.
Mistry et al., "Evidence of acceptability of oral paediatric medicines: a review," J. Pharm. Pharmacol. 2017, 69(4):361-376.
Mizuochi et al., "Characterization of urinary bile acids in a pediatric BRIC-1 patient: effect of rifampicin treatment," Clin Chim Acta. 2012, 413(15-16):1301-1304.
Moghadamrad et al., "Cholestasis in a patient with gallstones and a normal gamma-glutamyl transferase," Hepatology, 2013, 57(6):2539-2541.
Molly et al., "Development of a 5-step multi-chamber reactor as a simulation of the human intestinal microbial system," Appl. Microbiol. Biatechnol. 1993, 39:254-258.
Mowat et al., "Respiratory chain complex III [correction of complex] in deficiency with pruritus: a novel vitamin responsive clinical feature," J. Pediatr., 134(3):352-4, Mar. 1999.
Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.
Narchi et al., "Intrahepatic cholestasis in two omani siblings associated with a novel homozygous ATP8B1 mutation, c.379C>G (p.L127V)." Saudi J Gastroenterol. 2017, 23(5):303-305.
Neuman, et al., "Biomarkers in nonalcoholic fatty liver disease," Can. J. Gastroenterol. Hepatol. 2014, 28(11):607-618.
Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.
Noe et al., "Impaired expression and function of the bile salt export pump due to three novel ABCB11 mutations in intrahepatic cholestasis," J Hepatol. 2005, 43(3):536-543.
O'Neill et al.,"Comparison of efficacy of plant stanol ester and sterol ester: short-term and longer-term studies," American Journal of Cardiology, 96(1A):29d-36D, Jul. 2005.
Pai et al. Compression and evaluation of extended release matrix pellets prepared by the extrusion/spheronization process into disintegrating tablets. Brazilian Journal of Pharmaceutical Sciences. vol. 48, n. 1, janinnar., 2012 (Year: 2012).
Painter et al., "Sequence variation in the ATP8B1 gene and intrahepatic cholestasis of pregnancy," Eur J Hum Genet. 2005, 13(4):435-439.

(56) References Cited

OTHER PUBLICATIONS

Park et al., "Clinical and ABCB11 profiles in Korean infants with progressive familial intrahepatic cholestasis," World J Gastroenterol., 2016, 22(20):4901-4907.
Pauli-Magnus et al., "Enterohepatic transport of bile salts and genetics of cholestasis," Journal of Hepatology, 2005, 43(2):342-357.
Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.
Peng et al., "[Relationship between phenotype and genotype of ABCB11 deficiency in siblings and literature review].," Zhonghua er ke za zhi (Chinese journal of pediatrics) 2018, 56(6):440-444.
Qiu et al., "Defects in myosin VB are associated with a spectrum of previously undiagnosed low γ-glutamyltransferase cholestasis," Hepatology 2017, 65(5)1655-1669.
Reeder et al., "Quantitative assessment of liver fat with magnetic resonance imaging and spectroscopy," J Magn Reson Imaging. 2011, 34(4):729-749.
Renga et al., "Role of FXR in regulating bile acid homeostasis and relevance for human diseases," Curr. Drug. Targets Immune Endocr. Metabol. Disord., 5(3):289-303, Sep. 2005.
Rumbo et al., Transplantation 2018, vol. 102, No. 7, Supp. Supplement 1, pp. 5848. Abstract No. P.752. Meeting Info: 27th International Congress of The Transplantation Society, TTS 2018. Madrid, Spain. Jun. 30, 2018-Jul. 5, 2018.
Sanyal et al. The etiology of hepatocellular carcinonna and consequences of treatment. The Oncologist, 2010, 15 Suppl 4, 14-22.
Sattler et al., "Functional analysis of previously uncharacterised disease-causing mutations of the bile salt export pump," Journal of Hepatology 2017, 66(1):5177. Meeting Info.: International Liver Congress/ 52nd Annual Meeting of the European-Association-for-the-Studyof- the-Liver. Amsterdam, Netherlands. Apr. 19-23, 2017. European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-Gastroenterological Association. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Schumpelick et al., "[Ulcerative colitis—late functional results of ileoanal pouch anastomosis]," Chirung, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):5329. Abstract No. CO18. Meeting Info: 17th National Congress SIGENP. Pescara, Italy. Oct. 7, 2010-Oct. 9, 2010.
Shah et al., "Progressive Familial Intrahepatic Cholestasis Type 2 in an Indian Child," J Pediatr Genet. 2017, 6(2):126-127.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017. Bhubaneswar, india. Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile acid sequestrants and the treatment of type 2 diabetes mellitus," Drugs, 67(10):1383-92, 2007.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology. 2008, 134(4):1203-1214.
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Search Report for Swedish Appln. No. 1850915-8, dated Feb. 15, 2019, 2 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in Japanese patients with intrahepatic cholestasis associated with low gamma-glutamyl transpeptidase level," Journal of Pediatric Gastroenterology and Nutrition 2018, 67(1):5363, Abstract No. 615.
Treepongkaruna et al., "Novel ABCB11 mutations in a Thai infant with progressive familial intrahepatic cholestasis," World J Gastroenterol. 2009, 15(34):4339-4342.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Mil et al., "Benign recurrent intrahepatic cholestasis type 2 is caused by mutations in ABCB11," Gastroenterology. 2004, 127(2):379-384.
Varma et al., "Retargeting of bile salt export pump and favorable outcome in children with progressive familial intrahepatic cholestasis type 2," Hepatology 2015, 62(1):198-206.

(56) References Cited

OTHER PUBLICATIONS

Vaz et al., "Sodium taurocholate cotransporting polypeptide (SLC10A1) deficiency: conjugated hypercholanemia without a clear clinical phenotype," Hepatology, 2015, 61(1):260-267.

Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.

Waisbourd-Zinman et al., "A Rare BSEP Mutation Associated with a Mild Form of Progressive Familial Intrahepatic Cholestasis Type 2," Ann Hepatol. 2017, 16(3):465-468.

Walkowiak-Tomczak, "Characteristics of plums as a raw material with valuable nutritive and dietary properties—a review," Pol. J. Food Nutr. Sci., 58(4):401-405, 2008.

Walsh et al., "Patient acceptability, safety and access: A balancing act for selecting age-appropriate oral dosage forms for paediatric and geriatric populations," Int. J. Pharm. 2017, 536(2):547-562.

Wang et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.

Wang et al., "The Features of GGT in Patients with ATP8B1 or ABCB11 Deficiency Improve the Diagnostic Efficiency," PLoS One. 2016; 11(4):e0153114.

Wong et al., "Utility of oligonucleotide array-based comparative genomic hybridization for detection of target gene deletions," Clin Chem. 2008, 54(7)1141-1148.

Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.

Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.

Alvarez, "Development of crystallization processes for pharmaceutical applications," LACCEI, 2007, 2E.3-1-2E.3-9.

Chauhan et al., "Pharmaceutical polymers," Encycl. Biomed. Polymers and Polymeric Biomaterials, 2016, 5929-5942.

Gao et al., "Recent developments in the crystallization process: toward the pharmaceutical industry," Engineering, 2017, 3:343-353.

International Search Report and Written Opinion in Appln. No. PCT/SE2019/050603, dated Sep. 18, 2019, 11 pages.

Kolter et al., "Structure and dry binding activity of different polymers, including Kollidon VA 64," Drug Development, 2000, 26(11):1159-65.

Loh et al., "Overview of milling techniques for improving the solubility of poorly water-soluble drugs," Asian J Pharm Sci., 2015, 10:225-274.

Lopez et al., "Formulation approaches to pediatric oral drug delivery: benefits and limitations of current platforms," Expert Opin. Drug Deliv., 2015, 12(11):1727-1740.

Neuvonen et al., "Activated charcoal in the treatment of hypercholesterolaemia: dose-response relationships and comparison with cholestyramine," Eur J Clin Pharnnacol, 1989, 37(3):225.

Ricci, "Bridging studies in support of oral pediatric formulation development," Int. J. Pharmaceuticals, 2013, 457:323-326.

Swedish Office Action in Swedish Appln. No. 1850761-6, dated Dec. 17, 2018, 8 pages.

Swedish Office Action in Swedish Appln. No. 1850762-4, dated Dec. 27, 2018, 7 pages.

Swedish Search Report in Swedish Appln. No. 1850761-6, dated Dec. 17, 2018, 3 pages.

Swedish Search Report in Swedish Appln. No. 1850762-4, dated Dec. 27, 2018, 3 pages.

Tian et al., "Factors affecting crystallization of hydrates," J. Pharm. Pharmacol., 2010, 62:1534-1546.

\* cited by examiner

ORAL CHOLESTYRAMINE FORMULATION AND USE THEREOF

CROSS-REFERENCE TO RELATED APPLICATIONS

This application is a Continuation of U.S. application Ser. No. 15/449,779, filed Mar. 3, 2017, which is a Continuation under 35 U.S.C. § 111(a) of International Application No. PCT/SE2017/050128, filed Feb. 9, 2017, which claims priority to SE 1650157-9, filed Feb. 9, 2016. The disclosure of the foregoing applications are hereby incorporated by reference in their entirety.

TECHNICAL FIELD

The invention relates to an oral formulation for targeted delivery of cholestyramine to the colon, comprising a plurality of cholestyramine pellets that are coated with a diffusion-controlled inner coating and an enteric outer coating. The invention also relates to the use of this formulation in the treatment of bile acid malabsorption.

BACKGROUND

Bile acid malabsorption is a condition characterized by an excess of bile acids in the colon, often leading to chronic diarrhoea. Bile acids are steroid acids that are synthesized and conjugated in the liver. From the liver, they are excreted through the biliary tree into the small intestine where they participate in the solubilisation and absorption of dietary lipids and fat-soluble vitamins. When they reach the ileum, bile acids are reabsorbed into the portal circulation and returned to the liver. A small proportion of the secreted bile acids is not reabsorbed in the ileum and reaches the colon. Here, bacterial action results in deconjugation and dehydroxylation of the bile acids, producing the secondary bile acids deoxycholate and lithocholate.

In the colon, bile acids (in particular the dehydroxylated bile acids chenodeoxycholate and deoxycholate) stimulate the secretion of electrolytes and water. This increases the colonic motility and shortens the colonic transit time. If present in excess, bile acids produce diarrhoea with other gastrointestinal symptoms such as bloating, urgency and faecal incontinence. There have been several recent advances in the understanding of this condition of bile salt or bile acid malabsorption, or BAM (Pattni and Waltzes, *Br. Med. Bull.* 2009, vol 92, p. 79-93; Islam and Di Baise, *Pract. Gastroenterol.* 2012, vol. 36(10), p. 32-44). Dependent on the cause of the failure of the distal ileum to absorb bile acids, bile acid malabsorption may be divided into Type 1, Type 2 and Type 3 BAM. Diarrhoea may also be the result of high concentrations of bile acid in the large intestine following treatment with drugs that increase the production of bile acids and/or influence the reabsorption of bile acids by the small intestine, such as treatment with ileal bile acid absorption (IBAT) inhibitors.

The current treatment of bile acid malabsorption aims at binding excess bile acids in the gastrointestinal tract, beginning in the proximal part of the small bowel, thereby reducing the secretory actions of the bile acids. For this purpose, cholestyramine is commonly used as the bile acid sequestrant. Cholestyramine (or colestyramine; CAS Number 11041-12-6) is a strongly basic anion-exchange resin that is practically insoluble in water and is not absorbed from the gastrointestinal tract. Instead, it absorbs and combines with the bile acids in the intestine to form an insoluble complex. The complex that is formed upon binding of the bile acids to the resin is excreted in the faeces. The resin thereby prevents the normal reabsorption of bile acids through the enterohepatic circulation, leading to an increased conversion of cholesterol to bile acids to replace those removed from reabsorption. This conversion lowers plasma cholesterol concentrations, mainly by lowering of the low-density lipoprotein (LDL)-cholesterol.

Cholestyramine is also used as hypolipidaemic agents in the treatment of hypercholesterolemia, type II hyperlipoproteinaemia and in type 2 diabetes mellitus. It is furthermore used for the relief of diarrhoea associated with ileal resection, Crohn's disease, vagotomy, diabetic vagal neuropathy and radiation, as well as for the treatment of pruritus in patients with cholestasis.

In the current treatment of hyperlipidaemias and diarrhoea, the oral cholestyramine dose is 12 to 24 g daily, administered as a single dose or in up to 4 divided doses. In the treatment of pruritus, doses of 4 to 8 g are usually sufficient. Cholestyramine may be introduced gradually over 3 to 4 weeks to minimize the gastrointestinal effects. The most common side-effect is constipation, while other gastrointestinal side-effects are bloating, abdominal discomfort and pain, heartburn, flatulence and nausea/vomiting. There is an increased risk for gallstones due to increased cholesterol concentration in bile. High doses may cause steatorrhoea by interference with the gastrointestinal absorption of fats and concomitant decreased absorption of fat-soluble vitamins. Chronic administration may result in an increased bleeding tendency due to hypoprothrombinaemia associated with vitamin K deficiency or may lead to osteoporosis due to impaired calcium and vitamin D absorption. There are also occasional reports of skin rashes and pruritus of the tongue, skin and perianal region. Due to poor taste and texture and the various side effects, >50% of patients discontinue therapy within 12 months.

Another drawback with the current treatment using cholestyramine is that this agent reduces the absorption of other drugs administered concomitantly, such as oestrogens, thiazide diuretics, digoxin and related alkaloids, loperamide, phenylbutazone, barbiturates, thyroid hormones, warfarin and some antibiotics. It is therefore recommended that other drugs should be taken at least 1 hour before or 4 to 6 hours after the administration of cholestyramine. Dose adjustments of concomitantly taken drugs may still be necessary to perform.

In view of these side effects, it would be desirable if cholestyramine could be formulated as a colon release formulation, i.e. for release of the cholestyramine in the proximal part of the colon. Such a formulation may require a lower dose of cholestyramine and should have better properties regarding texture and taste, and may therefore be better tolerated by the patients. More importantly, colonic release of cholestyramine should be devoid of producing interactions with other drugs and should not induce risks for malabsorption of fat and fat-soluble vitamins, while still binding bile acids in order to reduce the increased colonic secretion and motility. For reasons of patient compliance, it would furthermore be desirable if the number of pills to be taken could be kept as low as possible. Each pill should therefore contain as much cholestyramine as possible.

EP 1273307 discloses preparations for preventing bile acid diarrhoea, comprising a bile acid adsorbent coated with a polymer so as to allow the release of the bile acid adsorbent around an area from the lower part of the small intestine to the cecum. It is shown that cholestyramine granules coated with HPMCAS-HF or ethyl cellulose displayed extensive swelling and bursting under conditions simulating the gastric environment.

Jacobsen et al. (*Br. Med. J.* 1985, vol. 290, p. 1315-1318) describe a study wherein patients who had undergone ileal resection were administered 500 mg cholestyramine tablets coated with cellulose acetate phthalate (12 tablets daily). In five of the 14 patients in this study, the tablets did not disintegrate in the desired place.

Despite progress made in this area, there still is a need for further improved cholestyramine formulations. In particular, there is a need for oral compositions for targeted delivery of cholestyramine to the colon.

BRIEF DESCRIPTION OF THE DRAWINGS

FIG. 1 shows the sequestration profiles for formulations A, B, and C in an assay simulating the pH of the stomach and the small intestine.

DETAILED DESCRIPTION OF THE INVENTION

Figure 1A:
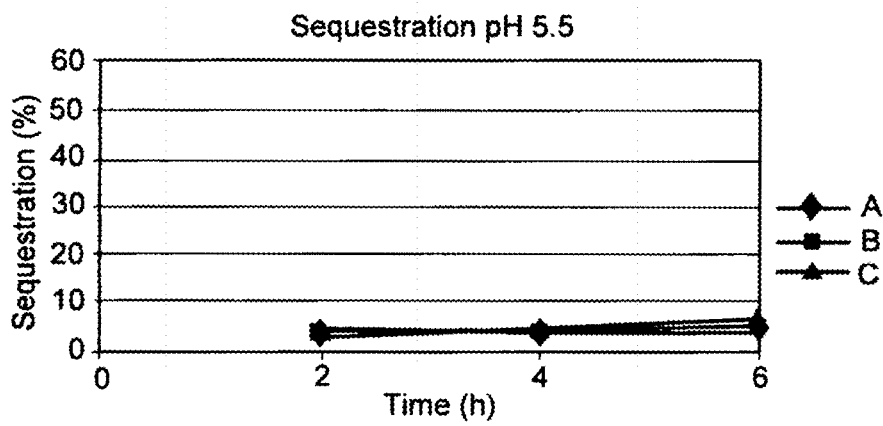
FIG. 1A shows the results for formulations A, B and C during 6 hours at pH 5.5.

It has been discovered that small and stable pellets of cholestyramine can be obtained, and that these pellets can be coated with a coating layer that prevents release of the pellets until they reach the colon. The combination of small cholestyramine pellets and a colon release coating allows the dose of cholestyramine to be reduced to for example 1.5 g twice daily. It is believed that this dose of cholestyramine is sufficient for binding an excess of bile acids in the colon. The composition disclosed herein further reduces undesired interactions of cholestyramine with other components in the gastrointestinal tract, such as other drugs or nutrients.

In one aspect, the invention relates to an oral formulation for targeted delivery of cholestyramine to the colon, comprising:
a) a plurality of pellets comprising cholestyramine;
b) a diffusion-controlled inner coating around said pellets; and
c) an enteric outer coating,
and wherein more than 70% of the cholestyramine is released in the colon.

The coating layers substantially prevent release of cholestyramine from the pellets until they reach the colon.

Preferably, more than 75% of the cholestyramine is released in the colon, such as more than 80%, or such as more than 85%. More preferably, more than 90% of the cholestyramine is released in the colon.

In another aspect, the invention relates to an oral formulation for targeted delivery of cholestyramine to the colon, comprising:
a) a plurality of pellets comprising cholestyramine;
b) a diffusion-controlled inner coating around said pellets; and
c) an enteric outer coating,
and wherein less than 30% of the cholestyramine is released in the small intestine.

Preferably, less than 25% of the cholestyramine is released in the small intestine, such as less than 20%, or such as less than 15%. More preferably, less than 10% of the cholestyramine is released in the small intestine.

The cholestyramine content of the pellets should be as high as possible. The uncoated pellets therefore preferably contain at least 70% w/w cholestyramine, more preferably at least 75% w/w cholestyramine, more preferably at least 80% w/w cholestyramine, even more preferably at least 85% w/w cholestyramine and most preferably at least 90% w/w cholestyramine.

In another aspect, the invention relates to an oral formulation for targeted delivery of cholestyramine to the colon, comprising:
a) a plurality of pellets comprising cholestyramine and
   i. at least 7% w/w of a vinylpyrrolidone-based polymer; or
   ii. a combination of at least 6% w/w of a vinylpyrrolidone-based polymer and at least 2% w/w of an acrylate copolymer; or
   iii. a combination of at least 5% w/w of a vinylpyrrolidone-based polymer and at least 3% w/w of an acrylate copolymer; or
   iv. a combination of at least 6% w/w of a vinylpyrrolidone-based polymer, at least 1% w/w of an acrylate copolymer and at least 10% w/w microcrystalline cellulose; or
   v. a combination of at least 5% w/w of a vinylpyrrolidone-based polymer, at least 2% w/w of an acrylate copolymer and at least 20% w/w microcrystalline cellulose;
b) a diffusion-controlled inner coating around said pellets; and
c) an enteric outer coating.

In one embodiment, more than 70% of the cholestyramine is released in the colon, preferably more than 75%, such as more than 80%, or such as more than 85%. More preferably, more than 90% of the cholestyramine is released in the colon.

In another embodiment, less than 30% of the cholestyramine is released in the small intestine, preferably less than 25%, such as less than 20%, or such as less than 15%. More preferably, less than 10% of the cholestyramine is released in the small intestine.

The presence of specific amounts of a vinylpyrrolidone-based polymer, or of a combination of a vinylpyrrolidone-based polymer and an acrylate copolymer, in the composition of the pellets allows for a high cholestyramine content. The resulting pellets are stable enough to withstand the conditions necessary for applying the coating layers onto the pellets.

The diffusion-controlled inner coating and the enteric outer coating substantially prevent release of cholestyramine from the pellets until they reach the large intestine, in particular the proximal colon. Additionally, the coating prevents the pellets from bursting. When water that diffuses through the coating is absorbed by the cholestyramine, the increasing volume of the cholestyramine leads to swelling of the pellets. The diffusion-controlled inner coating of the pellets is elastic and is therefore able to withstand the swelling of the pellets. The coating thereby prevents burst of the pellets and premature release of the cholestyramine.

Because of its very low solubility, cholestyramine is not "released" from the formulation in that it dissolves from the formulation and diffuses into the intestine. Instead, the cholestyramine probably stays within the gradually degrading structure of the coated pellet. Therefore, as used herein, the term "release" of the cholestyramine refers to the availability of the cholestyramine to the intestinal content in order to bind components (i.e., bile acids) therein.

Pellets

As used herein, the term "pellets" refers to extruded pellets, i.e. pellets obtained through extrusion and spheronization. The preparation of extruded pellets typically comprises the steps of mixing a powder with a liquid to obtain a wet mass, extruding the wet mass, spheronizing the extrudate and drying of the wet pellets.

It is essential that the pellets are stable enough to withstand mechanical stress during handling, such as during drying and coating of the pellets. The stability of the pellets may be expressed in terms of friability, which is the ability of a solid substance (such as a tablet, granule, sphere or pellet) to be reduced to smaller pieces, e.g. by abrasion, breakage or deformation. A low degree of friability means that the solid substance breaks into smaller pieces only to a low extent. As used herein, friability is defined as the reduction in the mass of the pellets occurring when the pellets are subjected to mechanical strain, such as tumbling, vibration, fluidization, etc. Methods for measuring friability are known in the art (e.g., European Pharmacopoeia 8.0, tests 2.9.7 or 2.9.41).

Experiments have shown that the inclusion of smaller amounts of vinylpyrrolidone-based polymer and/or acrylate copolymer than specified above results in lower yield and higher friability of the pellets. Although it is not possible to define acceptable friability limits for pellets in general, friability values of <1.7% w/w friability have been reported as acceptable to withstand stresses associated with fluid bed coating, handling and other processes (Vertommen and Kinget, *Drug Dev. Ind. Pharm.* 1997, vol. 23, p. 39-46). For the cholestyramine pellets of the present invention, it has been found that a friability of 2.1% is still acceptable. The friability is preferably lower than 2.0%, more preferably lower than 1.5%, and even more preferably lower than 1.0%.

The vinylpyrrolidone-based polymer in the pellets may be polyvinylpyrrolidone (povidone) or a vinylpyrrolidone-vinyl acetate copolymer (copovidone). Povidone is a linear, water-soluble polymer made from N-vinylpyrrolidone. Copovidone (also known as copolyvidone) is a linear, water-soluble copolymer of 1-vinyl-2-pyrrolidone (povidone) and vinyl acetate in a ratio of 6:4 by mass. In a preferred embodiment, the vinylpyrrolidone-based polymer is copovidone.

The acrylate copolymer in the pellets may be any pharmaceutically acceptable copolymer comprising acrylate monomers. Examples of acrylate monomers include, but are not limited to, acrylate (acrylic acid), methyl acrylate, ethyl acrylate, methacrylic acid (methacrylate), methyl methacrylate, butyl methacrylate, trimethylammonioethyl methacrylate and dimethylaminoethyl methacrylate. Several acrylate copolymers are known under the trade name Eudragit®.

Poly(ethyl acrylate-co-methyl methacrylate-co-trimethylammonioethyl methacrylate chloride) is a copolymer of ethyl acrylate, methyl methacrylate and a low content of trimethylammonioethyl methacrylate chloride (a methacrylic acid ester with quaternary ammonium groups). The copolymer is also referred to as ammonio methacrylate copolymer. It is insoluble but the presence of the ammonium salts groups makes the copolymer permeable. The copolymer is available as a 1:2:0.2 mixture (Type A) or as a 1:2:0.1 mixture (Type B). 30% aqueous dispersions of Type A and Type B are sold under the trade names Eudragit® RL 30 D and Eudragit® RS 30 D, respectively.

Poly(methyl acrylate-co-methyl methacrylate-co-methacrylic acid) 7:3:1 is a copolymer of methyl acrylate, methyl methacrylate and methacrylic acid. It is insoluble in acidic media but dissolves by salt formation above pH 7.0. A 30% aqueous dispersion is sold under the trade name Eudragit® FS 30 D.

Poly(methacrylic acid-co-ethyl acrylate) 1:1 is a copolymer of ethyl acrylate and methacrylic acid. It is insoluble in acidic media below a pH of 5.5 but dissolves above this pH by salt formation. A 30% aqueous dispersion is sold under the trade name Eudragit® L 30 D-55.

Further suitable acrylate copolymers include poly(ethyl acrylate-co-methyl methacrylate) 2:1, which is a water-insoluble copolymer of ethyl acrylate and methyl methacrylate. 30% aqueous dispersions are sold under the trade names Eudragit® NE 30 D and Eudragit® NM 30 D.

Preferred acrylate copolymers are ammonio methacrylate copolymer, poly(methyl acrylate-co-methyl methacrylate-co-methacrylic acid) 7:3:1, and poly(methacrylic acid-co-ethyl acrylate) 1:1. More preferably, the acrylate polymer is ammonio methacrylate copolymer, and most preferably the acrylate polymer is poly(ethyl acrylate-co-methyl methacrylate-co-trimethylammonioethyl methacrylate chloride) 1:2:0.2.

In one embodiment, the pellets comprise cholestyramine and
  i. at least 7% w/w of a vinylpyrrolidone-based polymer; or
  ii. a combination of at least 6% w/w of a vinylpyrrolidone-based polymer and at least 2% w/w of an acrylate copolymer.

In a more preferred embodiment, the pellets comprise cholestyramine and
  i. at least 7% w/w copovidone; or
  ii. a combination of at least 6% w/w copovidone and at least 2% w/w ammonio methacrylate copolymer.

The pellets may further comprise an excipient such as microcrystalline cellulose. In one embodiment, the pellets comprise from 0 to 20% w/w microcrystalline cellulose, such as from 0 to 10% w/w microcrystalline cellulose. In a more preferred embodiment, the pellets comprise from 0 to 5% w/w microcrystalline cellulose.

In another embodiment, the pellets are free from microcrystalline cellulose.

In one embodiment, the pellets comprise from 70 to 92% w/w cholestyramine, from 6 to 12% w/w of a vinylpyrrolidone-based polymer, from 2 to 5% w/w of an acrylate copolymer and from 0 to 20% w/w microcrystalline cellulose. More preferably, the pellets comprise from 80 to 92% w/w cholestyramine, from 6 to 12% w/w of a vinylpyrrolidone-based polymer, from 2 to 5% w/w of an acrylate copolymer and from 0 to 5% w/w microcrystalline cellulose.

In another embodiment, the pellets comprise from 70 to 92% w/w cholestyramine, from 6 to 12% w/w copovidone, from 2 to 5% w/w ammonio methacrylate copolymer and from 0 to 20% w/w microcrystalline cellulose. More preferably, the pellets comprise from 80 to 92% w/w cholestyramine, from 6 to 12% w/w copovidone, from 2 to 5% w/w ammonio methacrylate copolymer and from 0 to 5% w/w microcrystalline cellulose.

In another embodiment, the pellets comprise from 70 to 93% w/w cholestyramine, from 7 to 12% w/w of a vinylpyrrolidone-based polymer and from 0 to 20% w/w microcrystalline cellulose. More preferably, the pellets comprise from 70 to 93% w/w cholestyramine, from 7 to 12% w/w copovidone and from 0 to 20% w/w microcrystalline cellulose.

In yet another embodiment, the pellets comprise from 80 to 93% w/w cholestyramine, from 7 to 12% w/w of a vinylpyrrolidone-based polymer and from 0 to 10% w/w microcrystalline cellulose. More preferably, the pellets comprise from 80 to 93% w/w cholestyramine, from 7 to 12% w/w copovidone and from 0 to 10% w/w microcrystalline cellulose.

The uncoated pellets rapidly disintegrate under aqueous conditions. However, they are stable enough to withstand the conditions necessary for applying the colon release coating onto the pellets.

Diffusion-Controlled Coating

The diffusion-controlled inner coating provides a modified release of the cholestyramine, i.e. the cholestyramine is not made available at once but over an extended period of time. The coating comprises one or more polymers that are insoluble at any pH value, but that are permeable to water and small molecules dissolved therein. Examples of such polymers include, but are not limited to, poly(ethyl acrylate-co-methyl methacrylate-co-trimethylammonioethyl methacrylate chloride) 1:2:0.2 (Eudragit® RL 30 D), poly(ethyl acrylate-co-methyl methacrylate-co-trimethylammonioethyl methacrylate chloride) 1:2:0.1 (Eudragit® RS 30 D), poly(ethyl acrylate-co-methyl methacrylate) 2:1 (Eudragit® NE 30 D or Eudragit® NM 30 D) and polyvinyl acetate (Kollicoat® SR 30 D). The diffusion-controlled inner coating preferably comprises poly(ethyl acrylate-co-methyl methacrylate-co-trimethylammonioethyl methacrylate chloride) 1:2:0.2 (Eudragit® RL 30 D), poly(ethyl acrylate-co-methyl methacrylate-co-trimethylammonioethyl methacrylate chloride) 1:2:0.1 (Eudragit® RS 30 D) or a combination thereof, and most preferably poly(ethyl acrylate-co-methyl methacrylate-co-trimethylammonioethyl methacrylate chloride) 1:2:0.1.

When water is absorbed by the cholestyramine, the increasing volume of the cholestyramine leads to swelling of the pellets. The diffusion-controlled inner coating should therefore be elastic (i.e., have high elongation at break). Because of the elasticity of the coating, the coating is able to withstand this swelling. Burst of the pellets and premature release of the cholestyramine is thereby avoided. The elasticity of the coating may be the result of the elasticity of the organic polymer(s) itself, or may be induced by the addition of a plasticizer. Examples of suitable plasticizers include triethyl citrate, glyceryl triacetate, tributyl citrate, diethyl phthalate, acetyl tributyl citrate, dibutyl phthalate and dibutyl sebacate.

Enteric Coating

The enteric coating comprises a pH-sensitive polymer that is stable and insoluble at the acidic pH values found in the stomach (pH ~1-3) but that breaks down rapidly or becomes soluble at less acidic pH values, such as the pH values found in the small intestine (pH ~6 to 7). Examples of such pH-sensitive polymers include, but are not limited to, cellulose acetate phthalate, cellulose acetate succinate, hydroxypropyl methylcellulose acetate succinate, hydroxypropyl methylcellulose phthalate, poly(methacrylic acid-co-methyl methacrylate) 1:1 (Eudragit® L 100), poly(methacrylic acid-co-methyl methacrylate) 1:2 (Eudragit® S 100), poly(methacrylic acid-co-ethyl acrylate) 1:1 (Eudragit® L 100-55), poly(methyl acrylate-co-methyl methacrylate-co-methacrylic acid) 7:3:1 (Eudragit® FS 30 D), polyvinyl acetate phthalate, shellac, sodium alginate, and zein, as well as mixtures thereof. The enteric coating preferably comprises a pH-sensitive polymer selected from the group consisting of poly(methacrylic acid-co-methyl methacrylate) 1:1, hydroxypropyl methylcellulose acetate succinate and poly(methacrylic acid-co-methyl methacrylate) 1:2. The enteric coating most preferably comprises hydroxypropyl methylcellulose acetate succinate.

The diffusion controlled and enteric coatings may comprise one or more additives, such as acids and bases, plasticizers, glidants, and surfactants. Examples of suitable acids include organic acids such as citric acid, acetic acid, trifluoroacetic acid, propionic acid, succinic acid, glycolic acid, lactic acid, malic acid, tartaric acid, ascorbic acid, pamoic acid, maleic acid, hydroxymaleic acid, phenylacetic acid, glutamic acid, benzoic acid, salicylic acid, mesylic acid, esylic acid, besylic acid, sulfanilic acid, 2-acetoxybenzoic and, fumaric acid, toluenesulfonic acid, methanesulfonic acid, ethane disulfonic add and oxalic acid, and inorganic acids such as hydrochloric acid, hydrobromic acid, sulphuric acid, sulfamic acid, phosphoric acid and nitric acid. Examples of suitable bases include inorganic bases such as sodium bicarbonate, sodium hydroxide and ammonium hydroxide. Examples of suitable plasticizers include triethyl citrate, glyceryl triacetate, tributyl citrate, diethyl phthalate, acetyl tributyl citrate, dibutyl phthalate and dibutyl sebacate. Examples of suitable glidants include talc, glyceryl monostearate, oleic acid, medium chain triglycerides and colloidal silicon dioxide. Examples of suitable surfactants include sodium dodecyl sulfate, polysorbate 80 and sorbitan monooleate.

In order to improve the adherence of the coating layer onto the cholestyramine pellets, or in order to minimize the interaction between the coating layer and the cholestyramine in the pellets, a barrier coating may optionally be present as an additional layer between the pellets and the coating layer. A barrier coating may also be present when two different coating layers should be kept physically separated from each other. A particularly suitable material for the barrier coating is hydroxypropyl methylcellulose (HPMC).

A thin layer of a non-sticking agent may ultimately be applied to the coated pellets. This outer layer prevents the coated pellets from sticking together, e.g. during storage. Examples of suitable non-sticking agents include fumed silica, talc and magnesium stearate.

Together, the coating layers substantially prevent release of the cholestyramine from the pellets until they have reached the large intestine. Additionally, because of the properties of the polymer in the diffusion-controlled inner coating, the cholestyramine is made available to the large intestine only slowly and during a period of several hours. Preferably, there should be no exposure of the cholestyramine in the small intestine, whereas the exposure should be quick once the multiparticulates have passed the ileocecal valve. In one embodiment, less than 30% of the cholestyramine is released in the small intestine, such as less than 20%, such as less than 10%. In a more preferred embodiment, less than 5% of the cholestyramine is released in the small intestine. In another embodiment, more than 70% of the cholestyramine is released in the colon, such as more than 80%, such as more than 90%. In a more preferred embodiment, more than 95% of the cholestyramine is released in the colon.

The coating layers add further weight and volume to the pellets. The smaller the size of the pellets, the larger is the impact of the coating on the volume of the final formulation. However, for reasons of patient compliance, it is desirable that the total volume of the formulation is kept as low as possible. The coating layers should therefore be as thin as possible. Preferably, the amount of coating in the final formulation (on dry weight basis) is less than 40% w/w, and more preferably less than 35% w/w.

The cholestyramine content of the pellets should be as high as possible. The uncoated pellets therefore preferably contain at least 70% w/w cholestyramine, more preferably at least 75% w/w cholestyramine, more preferably at least 80% w/w cholestyramine, even more preferably at least 85% w/w cholestyramine and most preferably at least 90% w/w cholestyramine. The cholestyramine content of the final formulation (on dry weight basis) is preferably at least 50% w/w, and more preferably at least 55% w/w.

The size of the pellets is initially governed by the diameter of the screen used in the extrusion step. After the extrusion and spheronization steps, the pellets may be sieved to obtain a pellet fraction with a narrow size distribution. The diameter of the uncoated cholestyramine pellets is preferably from 500 µm to 3000 µm, more preferably from 750 µm to 2000 µm and even more preferably from 1000 to 1600 µm. In a most preferred embodiment, the diameter of the pellets is from 1000 to 1400 µm.

The cholestyramine pellets may be prepared in a process comprising the steps of:
 i) mixing the dry ingredients;
 ii) adding water, and optionally the acrylate copolymer, to obtain a wet mass;
 iii) extruding the wet mass;
 iv) spheronizing the extrudate; and
 v) drying the obtained pellets.

The dried pellets may thereafter be sieved in order to obtain pellets of uniform size.

The dry ingredients in step i) comprise cholestyramine and the vinylpyrrolidone-based polymer, and may optionally comprise microcrystalline cellulose.

Because of its physical nature, cholestyramine powder is able to absorb large amounts of water, which results in considerable swelling of the material. In order to prepare a wet mass from dry cholestyramine, it is therefore necessary to add more water than normally it would be used for preparing a wet mass from dry ingredients. Preferably, water is added to the mix of dry ingredients in an amount of at least 1.5 times the amount of cholestyramine (w/w), more preferably in an amount of at least 1.75 times the amount of cholestyramine (w/w), and even more preferably in an amount of at least 2 times the amount of cholestyramine (w/w).

The coating may be applied onto the cholestyramine pellets by methods known in the art, such as by film coating involving perforated pans and fluidized beds.

The oral formulation described herein may be administered to a patient in different forms, depending on factors such as the age and general physical condition of the patient. For example, the formulation may be administered in the form of one or more capsules wherein the coated pellets are contained. Such capsules conventionally comprise a degradable material, such as gelatin, hydroxypropyl methylcellulose (HPMC), pullulan or starch, which easily disintegrates under the acidic conditions in the stomach. The coated pellets are thereby quickly released into the stomach. Thus, in one aspect, the invention relates to a capsule comprising the oral formulation disclosed herein.

Alternatively, the coated pellets may be administered as a sprinkle formulation, the contents of which can be dispersed in liquid or soft food. Such a formulation does not require the swallowing of larger capsules and is therefore particularly useful for infants and small children as well as for older adults. Thus, in another aspect, the invention relates to a sprinkle formulation comprising the oral formulation disclosed herein. In such a formulation, the coated pellets may be contained within a capsule, sachet or stick pack.

The oral formulation disclosed herein provides several advantages over other formulations. The small coated pellets (multiparticulates) according to the present invention are able to easily pass the gastrointestinal tract. This eliminates the risk that the formulation is temporarily held up in the gastrointestinal tract, such as at the stomach or at the ileocecal valve, as is sometimes encountered with monolithic formulations (such as tablets or capsules that do not disintegrate in the stomach).

Furthermore, the cholestyramine is made available to the intestinal content only when the diffusion-controlled inner coating starts being degraded in the lower gastrointestinal tract, in particular the colon. The contents of the stomach and the small intestine are therefore effectively protected from the cholestyramine, which is a major improvement over formulations that directly release the cholestyramine in the stomach or the small intestine.

The low solubility of cholestyramine in aqueous environment prevents the release of cholestyramine from the formulation to be measured directly. The availability of the cholestyramine to the intestinal content over time and at different pH values can instead be determined in vitro, such as by measuring the sequestering capacity of the formulation under simulated conditions for the gastrointestinal tract. Such a method involves measuring the decreasing amount of free bile acid (i.e., the compound to be sequestered) in a liquid medium representative of the gastrointestinal tract, as described in the experimental section. See also the Official Monograph for cholestyramine resin (USP 40, page 3404).

In another aspect, the invention relates to the formulation disclosed herein for use in the treatment or prevention of bile acid malabsorption.

The invention also relates to the use of the formulation disclosed herein in the manufacture of a medicament for the treatment or prevention of bile acid malabsorption. The invention further relates to a method for the treatment or prevention of bile acid malabsorption comprising administering to a mammal in need of such treatment or prevention a therapeutically effective amount of the formulation disclosed herein.

Bile acid malabsorption may be divided into three different types, dependent on the cause of the failure of the distal ileum to absorb bile acids. Type 1 BAM is the result of (terminal) ileal disease (such as Crohn's disease) or (terminal) ileal resection or bypass. Type 2 BAM is often referred to as idiopathic bile acid malabsorption or primary bile acid diarrhoea (BAD) and is believed to be the result of an overproduction of bile acids or caused by a defective feedback inhibition of hepatic bile acid synthesis. This feedback regulation is mediated by the ileal hormone fibroblast growth factor 19 (FGF19) in man. Finally, type 3 BAM may be the result of cholecystectomy, vagotomy, small intestinal bacterial overgrowth (SIBO), coeliac disease, pancreatic insufficiency (chronic pancreatitis, cystic fibrosis), pancreatic transplant, radiation enteritis, collagenous colitis, microscopic colitis, lymphocytic colitis, ulcerative colitis or irritable bowel syndrome (i.e., diarrhoea-predominant irritable bowel syndrome (IBS-D)).

The formulation may also be used in combination with an Ileal Bile Acid Absorption (IBAT) inhibitor. Treatment with IBAT inhibitors, such as in the treatment of liver diseases, disorders of fatty acid metabolism or glucose utilization disorders, may result in increased levels of bile acids and/or influence the reabsorption of bile acids by the small intestine, leading to high concentrations of bile acid in the large intestine and thus causing diarrhoea. This side effect of the treatment with IBAT inhibitors may be treated or prevented by treatment with the formulation as disclosed herein. The formulation and the IBAT inhibitor may be administered simultaneously, sequentially or separately.

Thus, in another aspect, the invention relates to the formulation disclosed herein, for use in the treatment or prevention of diarrhoea upon oral administration of an IBAT inhibitor.

The invention also relates to the use of the formulation disclosed herein in the manufacture of a medicament for the treatment or prevention of diarrhoea upon oral administration of an IBAT inhibitor. The invention further relates to a method for the treatment or prevention of diarrhoea upon oral administration of an IBAT inhibitor, comprising administering to a mammal in need of such treatment or prevention therapeutically effective amounts of an IBAT inhibitor and of the formulation disclosed herein.

In a preferred embodiment, the invention relates to the formulation disclosed herein, for use in the treatment or prevention of bile acid diarrhoea upon treatment of a liver disease, such as a cholestatic liver disease, comprising oral administration of an IBAT inhibitor. In particular, the invention relates to the formulation disclosed herein for use in the treatment or prevention of diarrhoea upon treatment of Alagilles syndrome (ALGS), progressive familial intrahepatic cholestasis (PFIC), primary biliary cirrhosis (PBC), primary sclerosing cholangitis (PSC), autoimmune hepatitis, cholestatic pruritus, non-alcoholic fatty liver disease (NAFLD) or non-alcoholic steatohepatitis (NASH) comprising oral administration of an IBAT inhibitor.

In another embodiment, the invention relates to a method for the treatment or prevention of bile acid diarrhoea upon treatment of a liver disease comprising oral administration of an IBAT inhibitor, comprising administering to a mammal in need of such treatment or prevention a therapeutically effective amount of the formulation disclosed herein. In particular, the invention relates to such a method for the treatment or prevention of diarrhoea wherein the liver disease is Alagilles syndrome (ALGS), progressive familial intrahepatic cholestasis (PFIC), primary biliary cirrhosis (PBC), primary sclerosing cholangitis (PSC), autoimmune hepatitis, cholestatic pruritus, non-alcoholic fatty liver disease (NAFLD) or non-alcoholic steatohepatitis (NASH).

A liver disease as defined herein is any bile acid-dependent disease in the liver and in organs connected therewith, such as the pancreas, portal vein, the liver parenchyma, the intrahepatic biliary tree, the extrahepatic biliary tree, and the gall bladder. Liver diseases include, but are not limited to an inherited metabolic disorder of the liver; inborn errors of bile acid synthesis; congenital bile duct anomalies; biliary atresia; neonatal hepatitis; neonatal cholestasis; hereditary forms of cholestasis; cerebrotendinous xanthomatosis; a secondary defect of BA synthesis; Zellweger's syndrome; cystic fibrosis (manifestations in the liver); alpha1-antitrypsin deficiency; Alagilles syndrome (ALGS); Byler syndrome; a primary defect of bile acid (BA) synthesis; progressive familial intrahepatic cholestasis (PFIC) including PFIC-1, PFIC-2, PFIC-3 and non-specified PFIC; benign recurrent intrahepatic cholestasis (BRIC) including BRIC1, BRIC2 and non-specified BRIC; autoimmune hepatitis; primary biliary cirrhosis (PBC); liver fibrosis; non-alcoholic fatty liver disease (NAFLD); non-alcoholic steatohepatitis (NASH); portal hypertension; general cholestasis; jaundice during pregnancy; jaundice due to drugs; intrahepatic cholestasis; extrahepatic cholestasis; primary sclerosing cholangitis (PSC); gall stones and choledocholithiasis; malignancy causing obstruction of the biliary tree; pruritus due to cholestasis or jaundice; pancreatitis; chronic autoimmune liver disease leading to progressive cholestasis; hepatic steatosis; alcoholic hepatitis; acute fatty liver; fatty liver of pregnancy; drug-induced hepatitis; iron overload disorders; hepatic fibrosis; hepatic cirrhosis; amyloidosis; viral hepatitis; and problems in relation to cholestasis due to tumours and neoplasms of the liver, of the biliary tract and of the pancreas.

Disorders of fatty acid metabolism and glucose utilization disorders include, but are not limited to, hypercholesterolemia, dyslipidemia, metabolic syndrome, obesity, disorders of fatty acid metabolism, glucose utilization disorders, disorders in which insulin resistance is involved, and type 1 and type 2 diabetes mellitus.

IBAT inhibitors are often referred to by different names. As used herein, the term "IBAT inhibitors" should be understood as also encompassing compounds known in the literature as Apical Sodium-dependent Bile Acid Transporter Inhibitors (ASBTI's), bile acid transporter (BAT) inhibitors, ileal sodium/bile acid cotransporter system inhibitors, apical sodium-bile acid cotransporter inhibitors, ileal sodium-dependent bile acid transport inhibitors, bile acid reabsorption inhibitors (BARI's), and sodium bile acid transporter (SBAT) inhibitors.

IBAT inhibitors that can be used in combination with the bile acid sequestrant formulation disclosed herein include, but are not limited to, benzothiazepines, benzothiepines, 1,4-benzothiazepines, 1,5-benzothiazepines and 1,2,5-benzothiadiazepines.

Suitable examples of IBAT inhibitors that can be used in combination with the bile acid sequestrant formulation disclosed herein include, but are not limited to, the compounds disclosed in WO 93/16055, WO 94/18183, WO 94/18184, WO 96/05188, WO 96/08484, WO 96/16051, WO 97/33882, WO 98/03818, WO 98/07449, WO 98/40375, WO 99/35135, WO 99/64409, WO 99/64410, WO 00/47568, WO00/61568, WO 00/38725, WO 00/38726, WO 00/38727, WO 00/38728, WO 00/38729, WO 01/68096, WO 02/32428, WO 03/061663, WO 2004/006899, WO 2007/009655, WO 2007/009656, DE 19825804, EP 864582, EP 489423, EP 549967, EP 573848, EP 624593, EP 624594, EP 624595, EP 624596, EP 0864582, EP 1173205 and EP 1535913.

Particularly suitable IBAT inhibitors are those disclosed in WO 01/66533, WO 02/50051, WO 03/022286, WO 03/020710, WO 03/022825, WO 03/022830, WO 03/091232, WO 03/106482 and WO 2004/076430, and especially the compounds selected from the group consisting of:
1,1-dioxo-3,3-dibutyl-5-phenyl-7-methylthio-8-(N-{(R)-α-[N-(carboxymethyl)carbamoyl]-benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N'-((S)-1-carboxyethyl)carbamoyl]-benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N-((S)-1-carboxypropyl)-carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)-carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)-carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)-carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine;

or a pharmaceutically acceptable salt thereof.

Other particularly suitable IBAT inhibitors are those disclosed in WO99/32478, WO00/01687, WO01/68637, WO03/022804, WO 2008/058628 and WO 2008/058630, and especially the compounds selected from the group consisting of:

1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]-4-aza-1-azoniabicyclo[2.2.2]octane methanesulfonate;

1-[[4-[[4-[3,3-dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniazabicyclo[2.2.2]octane chloride;

1-[[5-[[3-[(3S,4R,5R)-3-butyl-7-(dimethylamino)-3-ethyl-2,3,4,5-tetrahydro-4-hydroxy-1,1-dioxido-1-benzothiepin-5-yl]phenyl]amino]-5-oxopentyl]amino]-1-deoxy-D-glucitol; and potassium ((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl)sulphate, ethanolate, hydrate.

An effective amount of the cholestyramine formulation according to the invention can be any amount containing more than or equal to about 100 mg of cholestyramine, such as more than or equal to about 250 mg, 500 mg, 750 mg, 1000 mg, 1250 mg, 1500 mg, 1750 mg or 2000 mg of cholestyramine. For example, the effective amount of cholestyramine can be between 100 mg and 5000 mg, such as between 250 mg and 2500 mg, between 250 mg and 2000 mg, between 500 mg and 2500 mg, between 500 mg and 2000 mg, or between 750 mg and 2000 mg.

A unit dose of the cholestyramine formulation according to the invention may comprise from 200 to 300 mg of cholestyramine, such as from 220 to 280 mg of cholestyramine, such as from 240 to 260 mg of cholestyramine. A unit dose preferably comprises about 250 mg of cholestyramine. The daily dose can be administered as a single dose or divided into one, two, three or more unit doses.

The frequency of administration of the formulation as disclosed herein can be any frequency that reduces the bile acid malabsorption condition without causing any significant adverse effects or toxicity to the patient. The frequency of administration can vary from once or twice a week to several times a day, such as once a day or twice a day. The frequency of administration can furthermore remain constant or be variable during the duration of the treatment.

Several factors can influence the frequency of administration and the effective amount of the formulation that should be used for a particular application, such as the severity of the condition being treated, the duration of the treatment, as well as the age, weight, sex, diet and general medical condition of the patient being treated.

The invention is further illustrated by means of the following examples, which do not limit the invention in any respect. All cited documents and references are incorporated herein by reference.

ABBREVIATIONS

HPLC High Performance Liquid Chromatography
PTFE Polytetrafluoroethylene
RH Relative humidity
rpm revolutions per minute
UHPLC Ultra High Performance Liquid Chromatography
UV-Vis Ultraviolet-visible spectroscopy

EXAMPLES

Example 1

Extrusion Experiments

All experiments were performed on a 100-200 g scale. The dry ingredients (cholestyramine, the vinylpyrrolidone-based polymer and/or microcrystalline cellulose) were mixed in the amounts indicated below. Water was added in portions of 50-100 gram with 3 minutes of mixing between each addition. When an acrylate copolymer was included in the experiment, it was added as a 2% w/w dispersion in water (20 g acrylate copolymer (aqueous dispersion 30%) added up to 300 g water). A final portion of pure water was added, if necessary. In each experiment, the total amount of liquid added was between 1.7 and 2.3 times the amount of solid material (w/w).

The wet mass was transferred to an extruder equipped with a 1.5 mm screen, operated at 25 rpm (revolutions per minute) and the extrudate was collected on a stainless steel tray. Approximately 100 g of the extrudate was run in the spheronizer for 1 minute at a speed of 730 rpm. The spheronized material was then transferred to stainless steel trays, placed in a drying oven and dried for 16 hours at 50° C. The yield was calculated as the fraction of pellets that pass through a 1.6 mm sieve but are retained on a 1.0 mm sieve.

Friability testing was performed using the equipment and procedure described in European Pharmacopoeia 8.0, test 2.9.7. The pellets were sieved on a 500 μm sieve to remove any loose dust before weighing.

The results using copovidone and Eudragit® RL 30 D are shown in Table 1, and the results using povidone and other Eudragit® copolymers are shown in Table 2.

TABLE 1

| | Amount (% w/w) | | | | | |
|---|---|---|---|---|---|---|
| Entry | Cholestyr-amine | Copovidone | MCC | Eudragit® RL 30 D | Yield (%) | Friability (%) |
| 1 | 100 | 0 | 0 | 0 | * | * |
| 2 | 90 | 0 | 10 | 0 | * | * |
| 3 | 70 | 0 | 30 | 0 | 39 | 1.6 |
| 4 | 70 | 6 | 24 | 0 | * | * |
| 5 | 70 | 0 | 26 | 4 | * | * |
| 6 | 70 | 6 | 20 | 4 | 85 | 0.1 |
| 7 | 80 | 3 | 15 | 2 | * | * |
| 8 | 85 | 7.5 | 4.5 | 3 | 92 | 0.6 |
| 9 | 90 | 6 | 4 | 0 | * | * |
| 10 | 90 | 0 | 6 | 4 | * | * |
| 11 | 90 | 0 | 0 | 10 | * | * |
| 12 | 90 | 6 | 0 | 4 | 85 | 1.4 |
| 13 | 90 | 10 | 0 | 0 | 87 | 1.2 |
| 14 | 91 | 9 | 0 | 0 | 82 | 0.5 |
| 15 | 92 | 8 | 0 | 0 | 83 | 1.5 |
| 16 | 93 | 7 | 0 | 0 | 78 | 1.0 |
| 17 | 94 | 6 | 0 | 0 | * | * |
| 18 | 91 | 6 | 0 | 3 | 84 | 0.3 |
| 19 | 92 | 6 | 0 | 2 | 82 | 1.6 |
| 20 | 93 | 6 | 0 | 1 | * | * |
| 21 | 85 | 6 | 8 | 1 | 81 | 3.5 |
| 22 | 80 | 6 | 13 | 1 | 85 | 0.8 |
| 23 | 92 | 5 | 0 | 3 | 70 | 2.0 |
| 24 | 93 | 5 | 0 | 2 | * | * |
| 25 | 85 | 5 | 8 | 2 | 54 | 7.1 |
| 26 | 80 | 5 | 13 | 2 | 73 | 9.1 |

* = extrusion followed by spheronization did not lead to pellets.

TABLE 2

| | Amount (% w/w) | | | | | |
|---|---|---|---|---|---|---|
| Entry | Cholestyr-amine | Povi-done | MCC | Eudragit® | Yield (%) | Friability (%) |
| 1 | 85 | 7.5 | 4.5 | 3% w/w FS 30 D | 79 | 0.2 |
| 2 | 85 | 7.5 | 4.5 | 3% w/w L 30 D-55 | 24 | 0.8 |
| 3 | 85 | 7.5 | 4.5 | 3% w/w NE 30 D | 88 | 0.5 |
| 4 | 85 | 7.5 | 4.5 | 3% w/w NM 30 D | 96 | 0.9 |
| 5 | 85 | 7.5 | 4.5 | 3% w/w RS 30 D | 82 | 0.8 |

Example 2

Preparation of Pellets

Pellets with a composition according to Table 1, entry 8, were manufactured at a batch size of 200 g in the extrusion step and 100 g in the spheronization step. 170 g cholestyramine, 15 g copovidone and 9 g microcrystalline cellulose were charged into a planetary mixer. The mixer was operated at intermediate speed and the liquid was slowly added in portions with mixing between each addition. First 300 g water with 20 g Eudragit® RL 30 D (30% dry weight) was added in three equal portions, with mixing for 3 minutes between each addition. Finally 40 g pure water was added and mixing was performed for additionally 30 seconds. The wet mass was then transferred to the extruder. The extruder was equipped with a 1.5 mm screen, operated at 25 rpm and the extrudate was collected on a stainless steel tray. Approximately 100 g of the extrudate was run in the spheronizer for 1 minute at a speed of 730 rpm. The spheronized material was then transferred to stainless steel trays, placed in a drying oven and dried for 16 hours at 50° C. The dried pellets were sieved and the fraction between 1 mm and 1.4 mm was collected.

Example 3

Formulations A-C for pH- and Diffusion-Controlled Release

The cholestyramine pellets of Example 2 were formulated with a colon release coating comprising an diffusion controlled inner coating based on poly(ethyl acrylate-co-methyl methacrylate-co-trimethylammonioethyl methacrylate chloride) and an enteric outer coating based on hydroxypropyl methylcellulose acetate succinate.

Three formulations were prepared with different amounts of poly(ethyl acrylate-co-methyl methacrylate-co-trimethylammonioethyl methacrylate chloride) in the inner coating, as follows:

Formulation A: 100% Eudragit® RL 30 D

Formulation B: 50% Eudragit® RL 30 D+50% Eudragit® RS 30 D

Formulation C: 100% Eudragit® RS 30 D

The pellets composition for a unit dose comprising 250 mg cholestyramine is shown below.

| Ingredient | Amount (mg/dose) |
|---|---|
| Cholestyramine | 250 |
| Copovidone (Kollidon® VA64 Fine) | 22.1 |
| Microcrystalline cellulose (Avicel® PH102) | 13.2 |
| Poly(ethyl acrylate-co-methyl methacrylate-co-trimethylammonioethyl methacrylate chloride) 1:2:0.2 (Eudragit® RL 30 D) | 8.8 |
| Total | 294.1 |

Inner Coating

A glycerol monostearate (GMS) emulsion containing GMS, polysorbate 80 and triethyl citrate was prepared according to general instructions from Evonik. The emulsion was mixed with Eudragit RL30D/RS30D dispersion (30% w/w). The composition of the inner coating film, based on dry weight, is shown below. The concentration, based on dry weight of the applied dispersion, is 19.8% (w/w).

| Ingredient<br>Inner coating | Amount<br>(w/w) |
|---|---|
| Poly(ethyl acrylate-co-methyl methacrylate-co-trimethylammonioethyl methacrylate chloride) 1:2:0.2 (Eudragit ® RL 30 D) or 1:2:0.1 (Eudragit ® RS 30 D) | 90.4 |
| Triethyl citrate | 4.5 |
| Glycerol monostearate 45-55 (Kolliwax ® GMS II) | 3.6 |
| Polysorbate 80 (Tween ® 80) | 1.5 |

The coating layer was applied using a Hüttlin Kugelcoater HKC005; batch size 75 g. The coating process was performed with an air inlet temperature of 45° C., resulting in a product temperature of 27-29° C. Air flow was adjusted to achieve an appropriate fluidization of the pellets during the coating. The coating was applied to the pellets so as to obtain a weight gain of 10%. After the coating, the pellets were heat-treated at 40° C. for 24 hours.

Outer Coating

The enteric coating was prepared by mixing 7% w/w hypromellose acetate succinate, 2.45% w/w triethyl citrate, 2.1% w/w talc, 0.21% w/w sodium lauryl sulphate and 88.24% w/w water for 30 min with an overhead stirrer at low temperature, <15° C. The composition of the outer coating film, based on dry weight, is shown below. The coating liquid was kept below 15° C. during the coating process.

| Ingredient<br>Outer coating | Amount<br>(w/w) |
|---|---|
| Hypromellose acetate succinate (AQOAT AS HF) | 59.5 |
| Triethyl citrate | 20.8 |
| Talc, micronized | 17.9 |
| Sodium lauryl sulphate (Kolliphor ® SLS Fine) | 1.8 |

The coating layer was applied using a Hüttlin Kugelcoater HKC005; batch size 75 g. The coating process was performed with an air inlet temperature of 55° C., resulting in a product temperature of 32° C. Air flow was adjusted to achieve an appropriate fluidization of the pellets during the coating. The enteric coating was applied to the pellets so as to obtain a weight gain of 40% (based on the weight of the coated pellets after application of the inner coating). After the coating, the pellets were heat-treated at 40° C./75% RH for 48 hours.

The coated pellets may be encapsulated in capsules, e.g. hard gelatine capsules. Details for the final formulations (on dry weight basis) are shown below:

Dose weight: 452.9 mg
Cholestyramine: 250 mg (55%)
Inner coating: 29.4 mg
Outer coating: 129.4 mg
Total coating: 158.8 mg (35%)

Example 4

Formulation D for pH- and Diffusion-Controlled Release

The cholestyramine pellets of Example 2 were formulated with a colon release coating comprising a diffusion controlled inner coating based on poly(ethyl acrylate-co-methyl methacrylate-co-trimethylammonioethyl methacrylate chloride), an enteric coating based on hydroxypropyl methylcellulose acetate succinate and finally coated with fumed silica to prevent sticking of the pellets during storage.

The pellets composition for a unit dose comprising 250 mg cholestyramine is shown below.

| Ingredient | Amount<br>(mg/dose) |
|---|---|
| Cholestyramine | 250 |
| Copovidone (Kollidon ® VA64 Fine) | 22.1 |
| Microcrystalline cellulose (Avicel ® PH102) | 13.2 |
| Poly(ethyl acrylate-co-methyl methacrylate-co-trimethylammonioethyl methacrylate chloride) 1:2:0.2 (Eudragit ® RL 30 D) | 8.8 |
| Total | 294.1 |

Inner Coating

A glycerol monostearate (GMS) emulsion containing GMS, polysorbate 80 and triethyl citrate was prepared according to general instructions from Evonik. The emulsion was mixed with Eudragit RS30D dispersion (30% w/w). The composition of the inner coating film, based on dry weight, is shown below. The concentration, based on dry weight of the applied dispersion, is 20.0% (w/w).

| Ingredient<br>Inner coating | Amount<br>(w/w) |
|---|---|
| Poly(ethyl acrylate-co-methyl methacrylate-co-trimethylammonioethyl methacrylate chloride) 1:2:0.1 (Eudragit ® RS 30 D) | 78.75 |
| Triethyl citrate | 15.75 |
| Glycerol monostearate 45-55 (Kolliwax ® GMS II) | 3.95 |
| Polysorbate 80 (Tween ® 80) | 1.55 |

The coating solution was applied using a Vector FL-M-1 apparatus. The initial batch size was 500 g. The coating process was performed with an air inlet temperature of 41-43° C., resulting in a product temperature of 28-30° C. The air flow was adjusted to achieve an appropriate fluidization of the pellets during the coating. The coating was applied to the cholestyramine pellets so as to obtain a weight gain of 10%. The coated pellets were then heat-treated at 40° C. for 50 hours and 30 minutes.

Enteric Coating

The enteric coating was prepared by mixing 7% w/w hypromellose acetate succinate, 2.45% w/w triethyl citrate, 2.1% w/w talc, 0.21% w/w sodium lauryl sulphate and 88.24% w/w water for 30 minutes with an overhead stirrer at low temperature, <15° C. The composition of the outer coating film, based on dry weight, is shown below. The coating liquid was kept below 15° C. during the coating process.

| Ingredient<br>Outer coating | Amount<br>(w/w) |
|---|---|
| Hypromellose acetate succinate (AQOAT AS HF) | 59.5 |
| Triethyl citrate | 20.8 |
| Talc, micronized | 17.9 |
| Sodium lauryl sulphate (Kolliphor ® SLS Fine) | 1.8 |

The coating layer was applied using a Vector FL-M-1 apparatus. The coating process was performed with an air inlet temperature of 35-55° C., resulting in a product temperature of 28-32° C. Air flow was adjusted to achieve an appropriate fluidization of the pellets during the coating. The enteric coating was applied to the pellets so as to obtain a weight gain of 40% (based on the weight of the coated pellets after application of the inner coating).

Final Coating

Directly after the enteric coating, fumed silica was applied onto the coated pellets by spraying a 5% suspension of Aerosil® 200 in water onto the pellets. The coating was applied using the same equipment with an inlet temperature of 40-41° C., resulting in a product temperature of 30° C. The air flow was adjusted to achieve an appropriate fluidization of the pellets during the coating. The coating was applied to the cholestyramine pellets so as to obtain a weight gain of 1% (w/w). The coated pellets were finally in-process heat-treated at 60° C. for 30 minutes in the coating equipment.

The coated pellets may be encapsulated in capsules, e.g. hard gelatine capsules. Details for the final formulations (on dry weight basis) are shown below:

Dose weight: 457.4 mg
Cholestyramine: 250 mg (55%)
　Inner coating: 29.4 mg
　Enteric coating: 129.4 mg
　Anti-sticking coating 4.5 mg
　Total coating: 163.3 mg (36%)

Example 5

Sequestration Assay

The sequestering capacities of formulations A, B and C were determined in a simplified assay, simulating the pH of the stomach and the small intestine. The sequestration was determined by measuring the decreasing amount of cholic acid in an aqueous solution. The USP Dissolution Apparatus 2 (paddle) Ph. Eur. 2.9.3 was used.

Sequestration at pH 5.5

An amount of formulation A, B or C corresponding to 250 mg cholestyramine was added to a vessel containing 500 mL of a buffered solution of cholic acid (0.192 mg/mL), pH 5.5 and the contents were stirred at 75 rpm for 6 hours. Samples of the solution were withdrawn at different time points and analysed for cholic acid by HPLC using a Thermo Hypersil Gold column, 50 mm×2.1 mm, particle size 1.9 μm; column temperature 60° C.; mobile phase 30:70 acetonitrile: phosphate buffer (pH 3.0); flow rate 0.75 mL/min. 5 replicate samples were analysed for each formulation and the average values were calculated.

Sequestration at pH 6.8 or 7.4

An amount of formulation A, B or C corresponding to 250 mg cholestyramine was added to a vessel containing 250 mL 0.1 M hydrochloric acid solution (pH 1) and the contents were stirred at 75 rpm for 2 hours. 250 mL of a solution of cholic acid in potassium hydroxide/potassium phosphate buffer solution was then added to the vessel, giving a buffered solution of cholic acid (0.192 mg/mL) with pH 6.8 or 7.4. After 1 minute of mixing, a first sample was removed. The pH was thereafter verified and if necessary adjusted to 6.8 or 7.4 by addition of the appropriate amount of 0.1 M potassium hydroxide solution. The solution was thereafter mixed for an additional 6 hours. Samples of the solution were withdrawn at different time points and analysed for cholic acid by HPLC using a Thermo Hypersil Gold column, 50 mm×2.1 mm, particle size 1.9 μm; column temperature 60° C.; mobile phase 30:70 acetonitrile: phosphate buffer (pH 3.0); flow rate 0.75 mL/min. 5 replicate samples were analysed for each formulation and the average values were calculated.

Figure 1B:
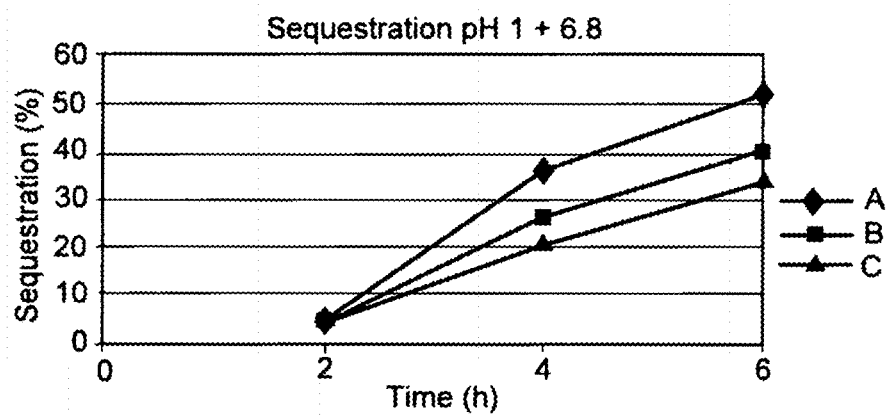
FIG. 1B shows the results during 2 hours at pH 1 followed by 4 hours at pH 6.8.
Figure 1C:
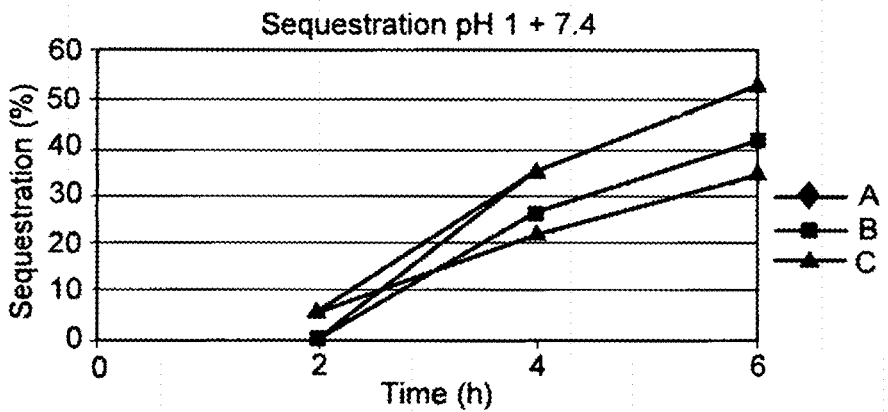
FIG. 1C shows the results for 2 hours at pH 1 followed by 4 hours at pH 7.4.

The sequestration profiles for formulations A-C are shown in FIG. 1. The pH of 5.5 is slightly lower than the pH normally observed in the duodenum, although it may occur in some patients and healthy persons. At this pH, sequestration is limited for all formulations (FIG. 1A). Sequestration at pH 6.8 is representative for the conditions in the ileum. At this pH, formulation A, B and C gave 52%, 42% and 34% sequestration, respectively, after 4 hours (FIG. 1B). At pH 7.4, formulation A, B and C gave 54%, 42% and 36% sequestration, respectively, after 4 hours (FIG. 1C). This pH is probably slightly higher than the pH normally observed in the distal ileum.

The coated pellets of formulations A, B and C showed no or only minor disintegration. Visual inspection of the pellets revealed that the coating was intact after stirring for 6 hours. In contrast, the uncoated pellets of Example 2, when stirred in a phosphate buffer (50 mM, pH 6.8) at 300 rpm (propeller stirrer), fully disintegrated within 1 minute and 25 seconds.

Example 6

In vitro Determination of the Sequestering Capacity of Formulations A-C under Simulated Conditions for the Gastrointestinal Tract The sequestering capacities of formulations A, B and C were studied in the Simulator of the Human Intestinal Microbial Ecosystem (SHIME®) as developed by ProDigest (Ghent, Belgium). The simulator was adapted to evaluate the sequestering capacity of binding bile salts under physiological conditions representative for fasted stomach, small intestine and proximal colon. The liquid media representative of the fasted stomach and small intestine have previously been described by Marzorati et al. (*LWT-Food Sci. Technol.* 2015, vol. 60, p. 544-551). The liquid medium for the proximal colon comprises a SHIME® matrix containing a stable microbial community representative for the human colon. A method for obtaining a stable microbial community of the human intestine is described by Possemiers et al. (*FEMS Microbiol. Ecol.* 2004, vol. 49, p. 495-507) and references therein. The sequestration was determined by measuring the decreasing amount of bile acids in an aqueous solution. A 40:40:20 (w/w) mixture of cholic acid (CA), chenodeoxycholic acid (CDCA) and deoxycholic acid (DCA) was used as a representative mixture of human bile salts (Carulli et al., *Aliment. Pharmacol. Ther.* 2000, vol. 14, issue supplement s2, p. 14-18).

A comparative experiment was conducted to which pure cholestyramine powder was added. A control experiment to which no cholestyramine was added was conducted in order to monitor the degradation of the bile salts under the colonic conditions used in the assay.

Each experiment was performed in triplicate to account for biological variation.

Fasted Stomach

Amounts of formulations A, B and C corresponding to 91 mg of cholestyramine and the pure cholestyramine (91 mg) were dosed to 14 mL fasted stomach liquid medium (pH 1.8). The digests were incubated for 1 hour at 37° C.

Small Intestine

After one hour of stomach incubation, 5.6 mL pancreatic juice (pH 6.8) containing the defined 40:40:20 mixture of bile salts (46.7 mM) was added. The small intestine digests were incubated for 2 hours at 37° C. and samples were taken after 0, 60 and 120 minutes.

Proximal Colon

After two hours of small intestine incubation, 42 mL of a full SHIME matrix (pH 6.0) originated from the ascending colon of a SHIME system was added. The colon digests were incubated for 24 hours at 37° C. and samples were collected every hour for the first 6 hours and then at 19h and at 24h.

Sample Analysis

The concentration of free bile salts in the samples was assessed by means of HPLC. A calibration curve was used to calculate the concentrations of CA, CDCA and DCA in the samples. One mL of each sample was centrifuged for 2 min at 5000 g. 500 μL of the supernatant was mixed with 500 μL of an 80:20 (v:v) mixture of methanol and phosphate buffer, vigorously vortexed, filtered through a 0.2 μm PTFE filter and injected in a Hitachi Chromaster HPLC equipped with a UV-Vis detector. The three bile salts were separated by a reversed-phase C18 column (Hydro-RP, 4 μm, 80 Å, 250×4.6 mm, Synergi). The separation was performed under isocratic conditions at room temperature, using a 80:20 (v:v) mixture of methanol and phosphate buffer as the mobile phase. The analysis was performed at 0.7 mL/min during 23 minutes and the bile salts were detected at 210 nm. The injection volume was set at 20 μL for stomach and small intestine samples and 50 μL for colon samples.

The full SHIME® matrix that was used for the colonic incubations contains (degraded) bile salts originating from BD Difco™ Oxgall, a dehydrated fresh bile extract from bovine origin (Catalog Number 212820). Although the exact composition of this mixture is unknown, a higher quantity of free bile salts might be expected in the colon samples. The values of the background (i.e. blank sample where no mix of bile salts was added) were therefore subtracted from each sample in order to take into account the 'baseline' of free bile salts present in the total SHIME® matrix.

The table below shows the relative concentrations of CA, CDCA and DCA, respectively, after 2 hours of small intestinal incubations ("SI-2") and after 4 hours of colonic incubations ("C-4"), as well as the proportional reduction in the period therebetween.

| | CA | | | CDCA | | | DCA | | |
|---|---|---|---|---|---|---|---|---|---|
| Formulation | SI-2 | C-4 | Δ | SI-2 | C-4 | Δ | SI-2 | C-4 | Δ |
| Control | 1 | 21 | 19 | 2 | 50 | 48 | 5 | 51 | 46 |
| Cholestyramine | 59 | 95 | 36 | 90 | 93 | 3 | 89 | 99 | 11 |
| A | 16 | 66 | 49 | 22 | 65 | 43 | 25 | 75 | 50 |
| B | 22 | 72 | 50 | 30 | 73 | 43 | 31 | 79 | 49 |
| C | 18 | 71 | 53 | 17 | 68 | 52 | 19 | 75 | 57 |

Figure 2:
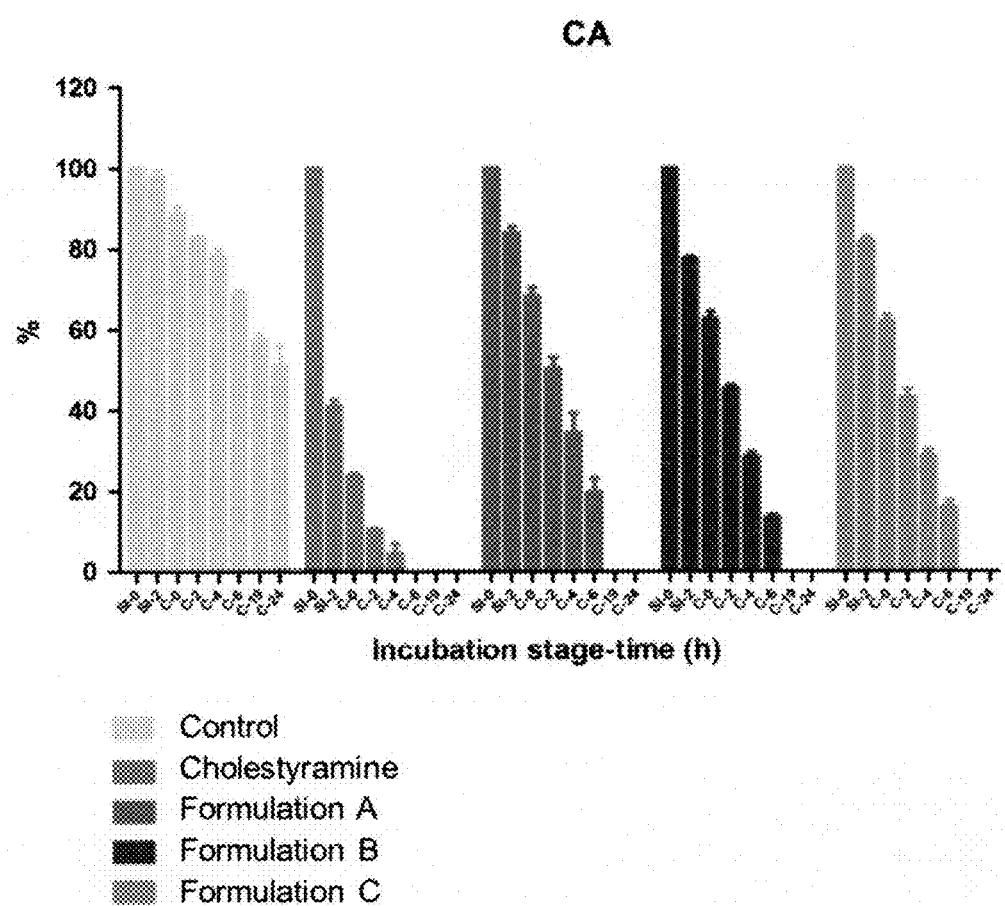
FIG. 2 shows the relative concentration of cholic acid (%) vs. incubation time (h) for formulations A, B and C in an in vitro SHIME® assay. The results for a comparative experiment using pure cholestyramine powder and a control experiment without cholestyramine are also shown.
Figure 3:
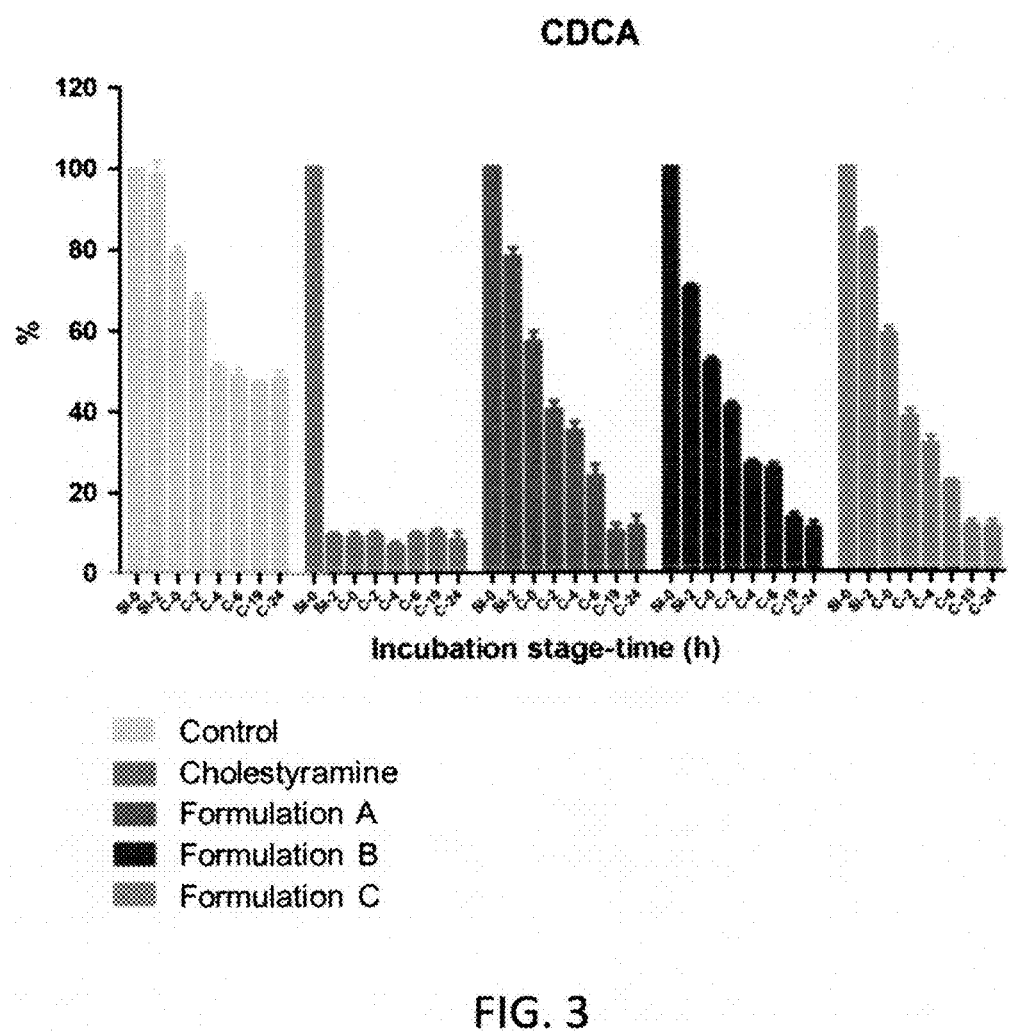
FIG. 3 shows the relative concentration of chenodeoxycholic acid (%) vs. incubation time (h) for formulations A, B and C in an in vitro SHIME® assay. The results for a comparative experiment using pure cholestyramine powder and a control experiment without cholestyramine are also shown.
Figure 4:
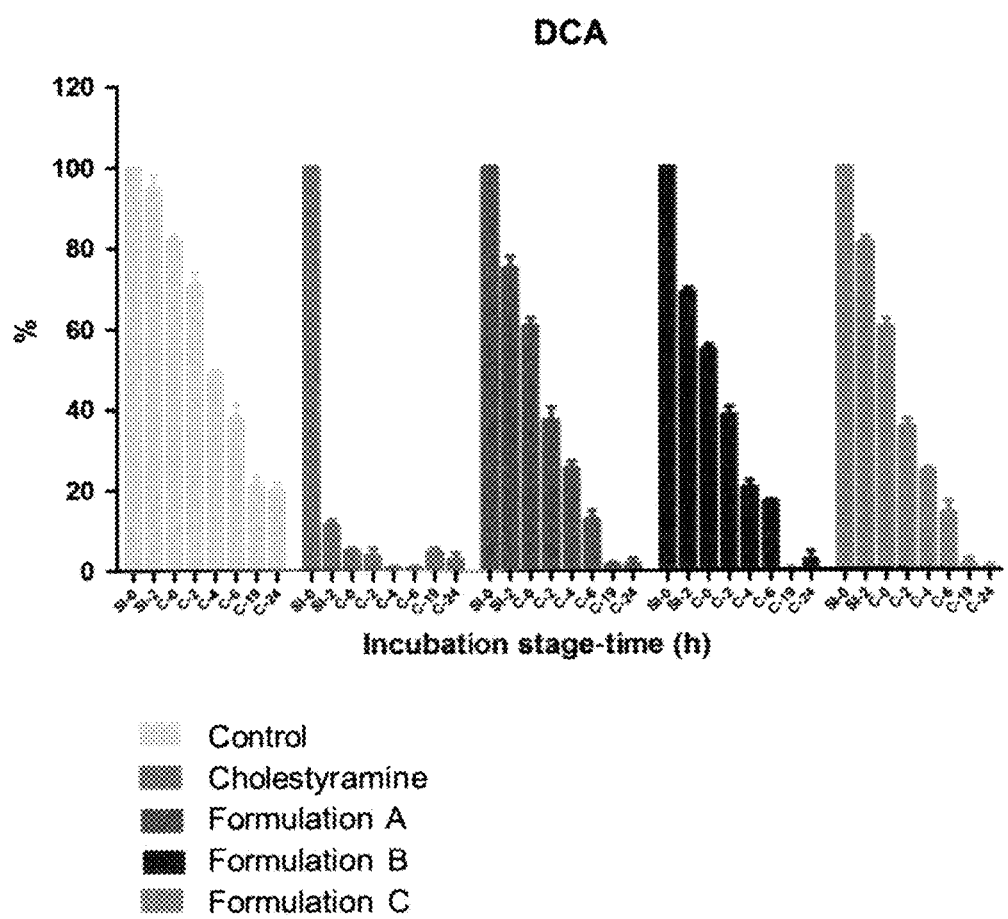
FIG. 4 shows the relative concentration of deoxycholic acid (%) vs. incubation time (h) for formulations A, B and C in an in vitro SHIME® assay. The results for a comparative experiment using pure cholestyramine powder and a control experiment without cholestyramine are also shown.

The relative concentrations of CA, CDCA and DCA (%) vs. incubation time are shown in FIGS. 2, 3 and 4, respectively. The graphs include the samples taken after 0 hours and 2 hours of small intestinal (SI) incubation, and after 0, 2, 4, 6, 19 and 24 hours of colonic (C) incubation.

The figures confirm the effect and extent of microbial salt metabolism in the gut (e.g. deconjugation, dehydrogenation and dehydroxylation) as observed by the significant decrease in bile salt levels in the control samples to which no cholestyramine was added.

It can be seen that the three formulations offered a protection of the active compound during the small intestinal incubation. Whereas pure (uncoated) cholestyramine led to a reduction of 59% of CA, 90% of CDCA and 89% of DCA already after 2 hours of small intestinal incubation (see the comparative experiment), formulations A, B and C gave rise to much lower reduction of bile salts during this period. During the small intestinal incubation, formulation C showed the best results, with only 18%, 17% and 19% reduction of CA, CDCA and DCA, respectively. During the first four hours of the colonic incubation, all three formulations gave rise to a large reduction of bile salts. Formulation C showed the best results, with 71% sequestration of CA, 68% sequestration of CDCA and 75% sequestration of DCA, corresponding to a 53%, 52% and 57% reduction of CA, CDCA and DCA, respectively.

Example 7

Stability Test

Hard capsules comprising formulation C (250 mg cholestyramine) were stored at 25° C./60% RH during 11 months.

After 0, 3, 6 and 11 months of storage, the capsules were analysed for cholestyramine and water content. Also, the sequestering capacity of the formulation was determined using the assay described in Example 5. The results are shown in the table below.

| | | Time (months) | | | |
|---|---|---|---|---|---|
| Analysis | Units | 0 | 3 | 6 | 11 |
| Cholestyramine content | mg/capsule | 250 | 246 | 245 | |
| | % of initial | 100 | 98.4 | 98.0 | |
| Water content | % | 18.3 | 17.8 | 16.9 | |
| Sequestration pH 5.5 (6 h) | % | 7 | 10 | 5 | 5 |
| Sequestration pH 1 (2 h) + pH 6.8 (4 h) | % | 34 | 35 | 36 | 36 |

The invention claimed is:

1. An oral dosage form comprising:
   a) a plurality of extruded and spheronized pellets, each extruded and spheronized pellet comprising a homogenous mixture of 70% to 93% w/w cholestyramine, at least 5% w/w of a vinylpyrrolidone-based polymer, at least 1% of an acrylate copolymer, and from 0 to 20% w/w of microcrystalline cellulose;
   b) a diffusion-controlled inner coating surrounding each extruded and spheronized pellet; and
   c) an enteric outer coating;
wherein the extruded and spheronized pellets exhibit a friability of less than 2.1% as measured using the European Pharmacopoeia 8.0, test 2.9.7.

2. The oral dosage form of claim 1, wherein the extruded and spheronized pellets exhibit a friability of less than 2%.

3. The oral dosage form of claim 2, wherein the extruded and spheronized pellets exhibit a friability of less than 1.5%.

4. The oral dosage form of claim 3, wherein the extruded and spheronized pellets exhibit a friability of less than 1.0%.

5. The oral dosage form of claim 1, wherein the extruded and spheronized pellets comprise at least 75% w/w cholestyramine.

6. The oral dosage form of claim 5, wherein the extruded and spheronized pellets comprise at least 80% w/w cholestyramine.

7. The oral dosage form of claim 6, wherein the extruded and spheronized pellets comprise at least 85% w/w cholestyramine.

8. The oral dosage form of claim 1, wherein the extruded and spheronized pellets comprise at least 90% w/w cholestyramine.

9. The oral dosage form of claim 1, wherein the vinylpyrrolidone-based polymer is copovidone.

10. The oral dosage form of claim 1, wherein the acrylate copolymer is an ammonio methacrylate copolymer.

11. The oral dosage form of claim 1, wherein the extruded and spheronized pellets comprise at least 10% w/w microcrystalline cellulose.

12. The oral dosage form of claim 1, wherein the extruded and spheronized pellets are free of microcrystalline cellulose and comprise at least 2% of an acrylate copolymer.

13. The oral dosage form of claim 1, wherein the diffusion-controlled inner coating is elastic.

14. The oral dosage form of claim 1, wherein the diffusion-controlled inner coating comprises poly(ethyl acrylate-co-methyl methacrylate-co-trimethylammonioethyl methacrylate chloride) 1:2:0.2, poly(ethyl acrylate-co-methyl methacrylate-co-trimethylammonioethyl methacrylate chloride) 1:2:0.1, or a combination thereof.

15. The oral dosage form of claim 1, wherein the enteric outer coating comprises hydroxypropyl methylcellulose acetate succinate.

16. The oral dosage form of claim 1, wherein the coating does not comprise hypromellose acetate succinate HF.

17. The oral dosage form of claim 1, wherein the coating does not comprise ethyl cellulose.

18. The oral dosage form of claim 1, wherein the coating does not comprise cellulose acetate phthalate.

19. The oral dosage form of claim 1, wherein the dosage form exhibits less than 20% sequestration of cholic acid after 6 hours at pH 5.5 as measured using a USP Dissolution Apparatus 2 (paddle) Ph. Eur. 2.9.3.

20. The oral dosage form of claim 1, wherein the dosage form exhibits greater than 30% sequestration of cholic acid after 2 hours at pH 1 followed by 4 hours at pH 6.8 as measured using a USP Dissolution Apparatus 2 (paddle) Ph. Eur. 2.9.3.

21. The oral dosage form of claim 20, wherein the dosage form exhibits less than 20% sequestration of cholic acid after 2 hours at pH 1 as measured using a USP Dissolution Apparatus 2 (paddle) Ph. Eur. 2.9.3.

22. The oral dosage form of claim 20, wherein the dosage form exhibits less than 10% sequestration of cholic acid after 2 hours at pH 1 as measured using a USP Dissolution Apparatus 2 (paddle) Ph. Eur. 2.9.3.

23. The oral dosage form of claim 1, wherein the dosage form exhibits greater than 30% sequestration of cholic acid after 2 hours at pH 1 followed by 4 hours at pH 7.4 as measured using a USP Dissolution Apparatus 2 (paddle) Ph. Eur. 2.9.3.

24. An oral dosage form comprising:
a) a plurality of extruded and spheronized pellets, each extruded and spheronized pellet comprising
70% to 93% w/w cholestyramine;
at least 5% w/w of a vinylpyrrolidone-based polymer;
at least 1% of an acrylate copolymer; and
from 0 to 20% w/w of microcrystalline cellulose,
wherein the cholestyramine, the vinylpyrrolidone-based polymer, the acrylate copolymer, a liquid, and, if present, the microcrystalline cellulose are combined to form a wet mass that is extruded and spheronized to form the plurality of extruded and spheronized pellets;
b) a diffusion-controlled inner coating surrounding each extruded and spheronized pellet, and
c) an enteric outer coating;
wherein the extruded and spheronized pellets exhibit a friability of less than 2.1% as measured using the European Pharmacopoeia 8.0, test 2.9.7.

25. The oral dosage form of claim 24, wherein the extruded and spheronized pellets comprise at least 75% w/w cholestyramine.

26. The oral dosage form of claim 24, wherein the vinylpyrrolidone-based polymer is copovidone.

27. The oral dosage form of claim 24, wherein the acrylate copolymer is an ammonio methacrylate copolymer.

28. The oral dosage form of claim 24, wherein the extruded and spheronized pellets comprise at least 10% w/w microcrystalline cellulose.

29. The oral dosage form of claim 24, wherein the extruded and spheronized pellets are free of microcrystalline cellulose and comprise at least 2% of an acrylate copolymer.

30. The oral dosage form of claim 24, wherein the dosage form exhibits less than 20% sequestration of cholic acid after 6 hours at pH 5.5 as measured using a USP Dissolution Apparatus 2 (paddle) Ph. Eur. 2.9.3.

* * * * *